US012584178B2

(12) United States Patent　　　(10) Patent No.: US 12,584,178 B2
Navarro López　　　　　　　　　　(45) Date of Patent: Mar. 24, 2026

(54) SALIVARY BIOMARKERS FOR THE DETECTION OF EPIDERMOID CANCER OF THE HEAD AND NECK

(71) Applicant: BIONOU RESEARCH S.L., San Juan de Alicante (ES)

(72) Inventor: Vicente Manuel Navarro López, San Vicente del Raspeig (ES)

(73) Assignee: BIONOU RESEARCH S.L., San Juan de Alicante (ES)

( * ) Notice: Subject to any disclaimer, the term of this patent is extended or adjusted under 35 U.S.C. 154(b) by 1070 days.

(21) Appl. No.: 17/601,382

(22) PCT Filed: Apr. 6, 2020

(86) PCT No.: PCT/EP2020/059761

§ 371 (c)(1),
(2) Date: Oct. 4, 2021

(87) PCT Pub. No.: WO2020/201575

PCT Pub. Date: Oct. 8, 2020

(65) Prior Publication Data

US 2022/0170111 A1　　Jun. 2, 2022

(30) Foreign Application Priority Data

Apr. 5, 2019　(EP) ..................................... 19382253

(51) Int. Cl.
| | |
|---|---|
| *C12Q 1/6886* | (2018.01) |
| *C12Q 1/689* | (2018.01) |
| *G01N 33/569* | (2006.01) |
| *G01N 33/574* | (2006.01) |

(52) U.S. Cl.
CPC ........... *C12Q 1/6886* (2013.01); *C12Q 1/689* (2013.01); *G01N 33/56955* (2013.01); *G01N 33/57407* (2013.01); *C12Q 2600/16* (2013.01); *G01N 2333/205* (2013.01)

(58) Field of Classification Search
CPC .................. C12Q 1/6886; C12Q 1/689; G01N 33/56911; G01N 33/57407
See application file for complete search history.

(56) References Cited

U.S. PATENT DOCUMENTS

2018/0010171 A1　1/2018　Mougeot et al.

FOREIGN PATENT DOCUMENTS

KR　10-2018-0003348 A　1/2018

OTHER PUBLICATIONS

Downes et al., Int J System Evolut Microbiol. 2013; 63: 1214-1218 (Year: 2013).*

Fernández Forné et al. Influence of the microbiome on radiotherapy-induced oral mucositis and its management: A comprehensive review. Oral Oncol. Sep. 2023;144:106488 (Year: 2023).*

Ganly et al. Periodontal pathogens are a risk factor of oral cavity squamous cell carcinoma, independent of tobacco and alcohol and human papillomavirus. Int J Cancer. Aug. 1, 2019;145(3):775-784. Epub Feb. 19, 2019 (Year: 2019).*

Gong et al. Microbiota in the Throat and Risk Factors for Laryngeal Carcinoma. Appl Environ Microbiol. Dec. 2014;80(23):7356-63. Epub Sep. 19, 2014 (Year: 2014).*

Hsaio et al., Carcinogenesis. Apr. 2018; 39(6): 778-787 (Year: 2018).*

Irfan, Delgado, and Frias-Lopez. The Oral Microbiome and Cancer. Front Immunol. Oct. 23, 2020; 11:591088. (Year: 2020).*

Lee et al. Bacterial alterations in salivary microbiota and their association in oral cancer. Sci Rep. Nov. 28, 2017;7(1):16540. (Year: 2017).*

Liu et al. Sex differences in the oral microbiome, host traits, and their causal relationships. iScience. Dec. 22, 2022;26(1):105839. (Year: 2022).*

Qin et al. Gender-specific microbial signatures in saliva: Unveiling the association between the oral microbiome and the pathogenesis of glioma. Heliyon. Aug. 31, 2024;10(17):e37284 (Year: 2024).*

Schmidt et al. Changes in Abundance of Oral Microbiota Associated with Oral Cancer. PLOS ONE. Jun. 2014; 9(6): e98741. (Year: 2014).*

Warnke-Sommer and Ali, "Evaluation of the oral microbiome as a biomarker for early detection of human oral carcinomas," 2017 IEEE International Conference on Bioinformatics and Biomedicine (BIBM), Kansas City, MO, USA, Nov. 2017, pp. 2069-2076 (Year: 2017).*

Wolf et al. The salivary microbiome as an indicator of carcinogenesis in patients with oropharyngeal squamous cell carcinoma: A pilot study. Sci Rep. Jul. 19, 2017;7(1):5867 (Year: 2017).*

Chun et al. The analysis of oral microbial communities of wild-type and toll-like receptor 2-deficient mice using a 454 GS FLX Titanium pyrosequencer. BMC Microbiol. Apr. 6, 2010;10:101 (Year: 2010).*

Kim et al. Enlarged superior cervical sympathetic ganglion mimicking a metastatic lymph node in the retropharyngeal space: a case report.Â J Korean Soc Radiol. 2017;76(4):278. (Year: 2017).*

Ferrazzano GF, et al. The effects of short-term consumption of commercial yogurt on salivary mutans streptococci and lactobacilli counts: an in vivo investigation. Eur J Clin Nutr. Oct. 2011;65(10):1170-2. Epub May 11, 2011 (Year: 2011).*

Cildir SK, et al. Reduction of salivary mutans streptococci in orthodontic patients during daily consumption of yoghurt containing probiotic bacteria. Eur J Orthod. Aug. 2009;31(4):407-11. Epub Feb. 4, 2009 (Year: 2009).*

(Continued)

*Primary Examiner* — Nancy J Leith
*Assistant Examiner* — Emma R Hoppe
(74) *Attorney, Agent, or Firm* — Seed Intellectual Property Law Group LLP

(57) ABSTRACT

Present invention relates to the in vitro use of the level or concentration in a salivary or breath sample of bacteria belonging to the *Alloprevotella, Prevotella, Campylobacter, Rothia, Catonella, Porphyromona, Fretibacterium* genus, or any combination thereof, for the diagnosis of carcinomas or epidermoid cancers, especially epidermoid cancer of the head and neck, in a patient, or to obtain useful data that allow such a diagnosis.

9 Claims, 17 Drawing Sheets

Specification includes a Sequence Listing.

(56)                 References Cited

OTHER PUBLICATIONS

Lin P, et al. Efficacy of probiotics in the treatment of oral mucositis in head and neck cancer patients: A systematic review and meta-analysis. Microb Pathog. Aug. 2024;193:106785 (Year: 2024).*

Schmidt BL, et al. Changes in abundance of oral microbiota associated with oral cancer. PLoS One. Jun. 2, 2014;9(6):e98741. (Year: 2014).*

Downes et al., "Description of *Alloprevotella rava* gen. nov., sp. nov., isolated from the human oral cavity, and reclassification of Prevotella tannerae Moore et al. 1994 as *Alloprevotella tannerae* gen. nov., comb. nov.," *International Journal of Systematic and Evolutionary Microbiology* 63:1214-1218, 2013.

Ganly et al., "Periodontal pathogens are a risk factor of oral cavity squamous cell carcinoma, independent of tobacco and alcohol and human papillomavirus," *International Journal of Cancer* 145:775-784, 2019.

Gong et al., "Microbiota in the Throat and Risk Factors for Laryngeal Carcinoma," *Applied and Environmental Microbiology* 80(23):7356-7363, Dec. 2014.

Hoorfar et al., "Making Internal Amplification Control Mandatory for Diagnostic PCR" *Journal of Clinical Microbiology* 41(12):5835, Dec. 2003.

Hsiao et al., "The interplay between oral microbiome, lifestyle factors and genetic polymorphisms in the risk of oral squamous cell carcinoma," *Carcinogenesis* 39(6):778-787, 2018.

Hurley et al., "Comparison of the salivary and dentinal microbiome of children with severe-early childhood caries to the salivary microbiome of caries-free children," *BMC Oral Health* 19(13), 2019. (14 pages).

Lim et al., "The Performance of an Oral Microbiome Biomarker Panel in Predicting Oral Cavity and Oropharyngeal Cancers," *Frontiers in Cellular and Infection Microbiology* 8(267), Aug. 2018. (9 pages).

Warnke-Sommer et al., "Evaluation of the oral microbiome as a biomarker for early detection of human oral carcinomas," *2017 IEEE International Conference on Bioinformatics and Biomedicine (BIBM)*, IEEE, Nov. 13, 2017, pp. 2069-2076. (8 pages).

Wolf et al., "The salivary microbiome as an indicator of carcinogenesis in patients with oropharyngeal squamous cell carcinoma: A pilot study," *Scientific Reports* 7(5867), Jul. 19, 2017. (10 pages).

Amer et al., "The Microbiome of Potentially Malignant Oral Leukoplakia Exhibits Enrichment for *Fusobacterium, Leptotrichia, Campylobacte,* and *Rothia* Species," *Frontiers in Microbiology* 8:2391, Dec. 1, 2017, (9 pages).

Pushalkar et al., "Comparison of oral microbiota in tumor and non-tumor tissues of patients with oral squamous cell carcinoma," *BMC Microbiology* 12:144, Jul. 20, 2012. (15 pages).

* cited by examiner

**Alloprevotella Genera
ROC CURVE**

The diagonal segments are produced by the draws

Fig. 7

Prevotella 7 Genera

CURVE

1-Specificity

The diagonal segments are produced by the draws

Campylobacter Genera

CURVE

The diagonal segments are produced by the draws

Rothia Genera

ROC CURVE

The diagonal segments are produced by the draws

Catonella Genera

ROC CURVE

1-Specificity

The diagonal segments are produced by the draws

Porphyromonas Genera

ROC CURVE

1-Specificity

The diagonal segments are produced by the draws

Fretibacterium Genera

ROC CURVE

1-Specificity

The diagonal segments are produced by the draws

SALIVARY BIOMARKERS FOR THE DETECTION OF EPIDERMOID CANCER OF THE HEAD AND NECK

STATEMENT REGARDING SEQUENCE LISTING

The Sequence Listing associated with this application is provided in text format in lieu of a paper copy, and is hereby incorporated by reference into the specification. The name of the text file containing the Sequence Listing is SEQUENCE_LISTING 150181_402USPC. The text file is 14.6 KB, was created on Oct. 4, 2021, and is being submitted electronically via EFS-Web.

TECHNICAL FIELD OF THE INVENTION

The present invention relates to a biomarker or a combination of biomarkers in salivary samples that, on the one hand, help to the diagnosis of Epidermoid Cancer of the Head and Neck and, on the other hand, predict the response to treatment of a subject with this disease.

STATE OF THE ART

Epidermoid Cancer of the Head and Neck is a malignant neoplastic entity originated in the epithelium that covers the mucosa of the aerodigestive tract. Its annual incidence of 700,000 patients places it in sixth positition of the world ranking in terms of more frequent cancers. Of the 53,640 new cases of head and neck tumours (oral cavity, pharynx and larynx) that were detected in the United States in 2013, 95% of them corresponded to epidermoid cancer of the head and neck. According to the 2010 GLOBOCAN Report, Spain is one of the countries with the highest incidence of epidermoid cancer of the head and neck in the entire European continent, proof of this are the 11,513 cases of patients with epidermoid cancer of the head and neck that were diagnosed in 2002.

In recent years, the use of saliva as a diagnostic tool or evolutionary follow-up of certain pathologies or diseases, has acquired great relevance in the field of biomedicine. The main advantage of the use of saliva as a diagnostic or follow-up tool is that consists on a non-invasive method, easy to collect, inexpensive, difficult to alter and stable under non-refrigerated conditions.

The human oral microbiota of which the salivary microbiota is also part comprises the set of microorganisms and pathogens that are components of the oral cavity. Its function is to protect the oral cavity and prevent the development of diseases. Recently, the use of massive sequencing techniques has allowed to study changes in the composition of the oral microbiota of healthy and sick patients. Some of the studies carried out so far, show that sites with oncological character have a lower diversity of species. Currently, the results of the salivary microbiota composition suggest that salivary species such as *Capnocytophaga gingivalis, Prevotelle melaninogenica*, and *Streptococcus Mitis* correlate with epidermoid cancer of the head and neck. Dysbiosis between epidermoid head and neck tumour sites and healthy tissues shows a decrease in Actinobacteria and Firmicutes phylo when compared with healthy tissues. However, analysis of the results at genus or species level does not show the same trend.

Epidermoid cancer of the head and neck is frequently diagnosed in advanced stages of the disease, conferring it a grim prognosis. At present, it seems paradoxical that, with the available means, there are no effective programs for the early detection of this type of tumours. In fact, between the genera proposed in the present invention as possible biomarkers with a predictive and diagnostic character (*Rothia, Prevotella, Alloprevotella, Campylobacter, Catonella, Porphylomona* and *Fretibacterium*), *Rothia* is the only one that has been used as an oral biomarker with clinical indications for carcinoma detection in the oral and oropharyngeal cavity until now [Lim Y, Fukuma N, Totsika M, Kenny L, Morrison M, Punyadeera C: The Performance of an Oral Microbiome Biomarker Panel in Predicting Oral Cavity and Oropharyngeal Cancers. Front Cell Infect My 2018, 8].

Thus, we understand that there is still a need to provide useful programs and tools for the early detection of epidermoid cancer of the head and neck.

DESCRIPTION OF THE INVENTION

Throughout the present invention, we analyze the diagnostic and prognostic capacity of the salivary microbiota, to be used as a biomarker for pharyngolaryngeal epidermoid cancer. With this purpose, a clinical study with sample collection at the "Bioithas" clinical research center (Alicante) was carried out. The statistical analysis was performed using the software SPSS © 15.0 and consisted of one descriptive part and another inferential part ("Chi square" test for qualitative variables and "Student's T" for quantitative variables). Spearman's "S" correlation was used for nonparametric samples. Finally, to study the validity of salivary microbiota values as a diagnostic and prognostic proof, ROC curves were used to calculate the most appropriated cut-off points together with their corresponding sensitivity and specificity values.

A total of 40 salivary samples corresponding to 20 patients and 20 healthy controls were included in the study. Among the patients, the average age was 61.9 years (minimum of 38 and maximum of 86). Most of them were male (98.7%), with a male/female ratio of 19 to 1, all patients were at the time of diagnosis in advanced stages of the disease (60.0%). The laryngeal location was the most frequently affected (85%).

Profiles of the salivary microbiota, comparative between cases and controls, and areas under the ROC curve for the main germs involved are described in the figures of the present invention. FIGS. 6 to 13 and table 3 show the different areas under the curve for each of the genera that showed statistically significant differences between groups in the present study. From this information, is possible to conclude that:

In case of both absolute values and percentage of presence of *Alloprevotella* genus in salivary samples and, especially, of its *Alloprevotella rava* and *Alloprevotella tannerae* species, there is a negative correlation between subjects with epidermoid cancer of the mouth and pharynx and healthy subjects;

In case of both absolute values and percentage of presence of *Prevotella* genus in salivary samples, there is a negative correlation between subjects with epidermoid cancer of the mouth and pharynx and healthy subjects;

In case of both absolute values and percentage of presence of *Campylobacter* genus in salivary samples, there is a negative correlation between subjects with epidermoid cancer of the mouth and pharynx and healthy subjects;

In case of both absolute values and percentage of presence of *Rothia* genus in salivary samples, there is a positive correlation between subjects with epidermoid cancer of the mouth and pharynx and healthy subjects;

In case of both absolute values and percentage of presence of *Catonella* genus in salivary samples, there is a negative correlation between subjects with epidermoid cancer of the mouth and pharynx and healthy subjects;

In case of both absolute values and percentage of presence of *Porphyromona* genus in salivary samples; there is a negative correlation between subjects with epidermoid cancer of the mouth and pharynx and healthy subjects; and In case of both absolute values and percentage of presence of *Fretibacterium* genus in salivary samples, there is a negative correlation between subjects with epidermoid cancer of the mouth and pharynx and healthy subjects.

Therefore, it can be conclude that on the one hand salivary microbiota shows high potential as a prognostic and diagnostic marker for the development of screening programs helping to the early diagnosis of epidermoid cancer of the head and neck in high-risk patients, and on the other hand it has potential to diagnose and predict both evolution and follow-up of patients with epidermoid cancer of the head and neck, being able to complement the known classic diagnostic/prognostic factors.

It is noted that, in the context of the present invention, *Alloprevotella* genus and, especially, its *Alloprevotella rava* and *Alloprevotella tannerae* species, are at lower levels in salivary biological samples of patients with epidermoid cancer of the head and neck than in general population. Furthermore, it is noted that the following sequences SEQ ID NO 1 to SEQ ID NO 3, are representative sequences of this genus and, therefore, useful for identification of bacteria belonging to this genus in such samples through a PCR procedure or by means of any sequencing technique, being of special interest the molecular diagnostic techniques by microarray.

-continued

```
ACTCCAATCGCGAAGGCAGGTGTCCGGGCTGCAACTGACGCTGAGGCTCG

AAAGTGTGGGTATCAAAC
```

```
                                              SEQ ID NO 3
>566e492fc8c692afeb1e84a3baeb42ad
AGGAATATTGGTCAATGGACGGAAGTCTGAACCAGCCAAGTAGCGTGCAG

GATGACGGCCCTCTGGGTTGTAAACTGCTTTTAGTTGGGAATAAAAAAGA

GGACGTGTCCTCTATTGTATGTACCTTCAGAAAAAGGACCGGCTAATTCC

GTGCCAGCAGCCGCGGTAATACGGAAGGTCCAGGCGTTATCCGGATTTAT

TGGGTTTAAAGGGAGCGTAGGCGGATTATTAAGTCAGTGGTGAAAGACGG

TGGCTCAACCATCGTTAGCCATTGAAACTGGTAGTCTTGAGTGCAGACAG

GGATGCTGGAACTCGTGGTGTAGCGGTGAAATGCTTAGATATCACGATGA

ACTCCGATCGCGAAGGCAGGTGTCCGGGCTGCAACTGACGCTGAGGCTCG

AAAGTGTGGGTATCAAAC
```

Other representative sequences of this genus will be known by the person skilled in the art and they will serve to identify those bacteria belonging to this genus in a saliva or breath sample.

On the other hand, it is noted that, in the context of the present invention, *Prevotella* genus is at lower levels in salivary biological samples of patients with epidermoid cancer of the head and neck than in general population. Furthermore, it is noted that the following sequences SEQ ID NO 4 to SEQ ID NO 6, are representative sequences of this genus and, therefore, useful for the identification of bacteria belonging to this genus in such samples through PCR or any other sequencing technique, including the molecular diagnostic techniques used by DNA microarray.

```
                                              SEQ ID NO 1
>d643812b99d154c919c0ce6b382a6d32
AGGAATATTGGTCAATGGACGGAAGTCTGAACCAGCCAAGTAGCGTGCAG

GATGACGGCCCTCTGGGTTGTAAACTGCTTTTAGTTGGGAATAAAAAAGA

GGACGTGTCCTCTATTGTATGTACCTTCAGAAAAAGGACCGGCTAATTCC

GTGCCAGCAGCCGCGGTAATACGGAAGGTCCAGGCGTTATCCGGATTTAT

TGGGTTTAAAGGGAGCGTAGGCGGATTATTAAGTCAGTGGTGAAAGACGG

TGGCTCAACCATCGTTAGCCATTGAAACTGGTAGTCTTGAGTGCAGACAG

GGATGCTGGAACTCGTGGTGTAGCGGTGAAATGCTTAGATATGACGAAGA

ACTCCGATTGCGAAGGCAGCTGACGGGAGCGCAACTGACGCTTAAGCTCG

AAGGTGCGGGTATCAAAC
```

```
                                              SEQ ID NO 2
>be884fc0a4b0abb13e06f9da1978b834
AGGAATATTGGTCAATGGACGGAAGTCTGAACCAGCCAAGTAGCGTGCAG

GATGACGGCCCTCTGGGTTGTAAACTGCTTTTAGTTGGGAATAAAAAAGA

GGACGTGTCCTCTATTGTATGTACCTTCAGAAAAAGGACCGGCTAATTCC

GTGCCAGCAGCCGCGGTAATACGGAAGGTCCAGGCGTTATCCGGATTTAT

TGGGTTTAAAGGGAGCGTAGGCGGATTATTAAGTCAGTGGTGAAAGACGG

TGGCTCAACCATCGTTAGCCATTGAAACTGGTAGTCTTGAGTGCAGACAG

GGATGCTGGAACTCGTGGTGTAGCGGTGAAATGCTTAGATATCACGATGA
```

```
                                              SEQ ID NO 4
>29971068736dbb4328b226203638d02e
GGGAATATTGCACAATGGGGGAAACCCTGATGCAGCAACGCCGCGTGAAC

GATGAAGGCCTTTGGGTCGTAAAGTTCTGTTCTAGGTGATGAAAACTGAC

AGTAACCTAGGAGAAAGCCCCGGCTAACTCCGTGCCAGCAGCCGCGGTAA

TACGGAGGGGGCAAGCGTTATCCGGATTTATTGGGTTTAAAGGGAGCGTA

GGCCGTAGATTAAGCGTGTTGTGAAATGTAGATGCTCAACATCTGACTTG

CAGCGCGAACTGGTTTACTTGAGTGTGCGCAACGTAGGCGGAATTCGTCG

TGTAGCGGTGAAATGCTTAGATATGACGAAGAACTCCGATTGCGAAGGCA

GCTTACGGGAGCACAACTGACGCTGAAGCTCGAAGGTGCGGGTATCAAAC
```

```
                                              SEQ ID NO 5
>c6ed086de07dcb19c3164e681606b792
GGGAATATTGCACAATGGAGGAAACTCTGATGCAGTGACACCGCGTATAG

GAAGAAGGTCTTAGGATTGTAAGCTATTGTCGTGTGAGAAGAAAATGACC

ATCACAGGAGGAAGCCCTGGCTAAATATGTGCCAGCAGCCGCGGTAATAC

GGAAGGTCCGGGCGTTATCCGGATTTATTGGGTTTAAAGGGAGCGTAGGC

CGTGGATTAAGCGTGTTGTGAAATGCAGGTGCTCAACGTCTGCACTGCAG

CGCGAACTGGTTCACTTGAGTGTGCACAACGCAGGCGGAATTCGTCGTGT

AGCGGTGAAATGCTTAGATATGACGAAGAACTCCGATTGCGAAGGCAGCT

TGCGGGAGCACAACTGACGCTGAAGCTCGAAAGTGCGGGTATCGAAC
```

-continued

SEQ ID NO 6

>6a4ca61245b7dfbbc3d341b72b017eca
GGGAATATTGGACAATGGGGGCAACCCTGATCCAGCAATTCTGTGTGCAC

GATGAAGGTCTTCGGATTGTAAAGTGCTTTCAGCAGGGAAGAAAAAAATG

ACGGTACCTGCAGAAGAAGCGACGGCTAAATACGTGCCAGCAGCCGCGGT

AATACGGAAGGTCCAGGCGTTATCCGGATTTATTGGGTTTAAAGGGAGTG

TAGGCGGTTTGTTAAGCGTGTTGTGAAATTTAGATGCTCAACATTTAACT

TGCAGCGCGAACTGTCAGACTTGAGTACACGCAACGTATGCGGAATTCAT

GGTGTAGCGGTGAAATGCTTAGATATCATGAAGAACTCCGATTGCGAAGG

CAGCATACGGGAGTGTAACTGACGCTTAAGCTCGAAGGTGCGGGTATCGA

AC

Other representative sequences of this genus will be known by the person skilled in the art and they will serve to identify those bacteria belonging to this genus in a saliva or breath sample.

Furthermore, it is noted that, in the context of the present invention, the *Campylobacter* genus is at lower levels in salivary biological samples of patients with epidermoid cancer of the head and neck than in general population. Furthermore, it is noted that the following sequences SEQ ID NO 7 to SEQ ID NO 9, are representative sequences of this genus and, therefore, useful for the identification of bacteria belonging to this genus in such samples through PCR or any other sequencing technique.

SEQ ID NO 7

>9eae616717ec194797c56f02fab79102
GGGAATATTGCTCAATGGGGGAAACCCTGAAGCAGCAACGCCGCGTGGAG

GATGACACTTTTCGGAGCGTAAACTCCTTTTCTTGGGGAAGAAATTTGAC

GGTACCCAAGGAATAAGCACCGGCTAACTCCGTGCCAGCAGCCGCGGTAA

TACGGAGGGTGCAAGCGTTACTCGGAATCACTGGGCGTAAAGGACGCGTA

GGCGGATTATCAAGTCTCTTGTGAAATCCAATGGCTTAACCATTGAACTG

CTTGGGAAACTGATAATCTAGAGTGAGGGAGAGGCAGATGGAATTGGTGG

TGTAGGGGTAAAATCCGTAGAGATCACCAGGAATACCCATTGCGAAGGCG

ATCTGCTGGAACTCAACTGACGCTAATGCGTGAAAGCGTGGGGAGCAAAC

SEQ ID NO 8

>69552d32bb95376b080521fcc96eca94
GGGAATATTGCTCAATGGGGGAAACCCTGAAGCAGCAACGCCGCGTGGAG

GATGACACTTTTCGGAGCGTAAACTCCTTTTCTTGGGGAAGAAATTTGAC

GGTACCCAAGGAATAAGCACCGGCTAACTCCGTGCCAGCAGCCGCGGTAA

TACGGAGGGTGCAAGCGTTACTCGGAATCACTGGGCGTAAAGGACGCGTA

GGCGGATTATCAAGTCTCTTGTGAAATCCAATGGCTTAACCATTGAACTG

CTTGGGAAACTGATAATCTAGAGTGAGGGAGAGGCAGATGGAATTGGTGG

TGTAGGGGTAAAATCCGTAGAGATCACCAGGAATACCCATTGCGAAGGCG

ATCTGCTGGAACTCAACTGACGCTAATGCGCGAAAGCGTGGGGAGCAAAC

SEQ ID NO 9

>3aad30e1911d0042c5a63850975b0af4
GGGAATATTGCTCAATGGGGGAAACCCTGAAGCAGCAACGCCGCGTGGAG

GATGACACTTTTCGGAGCGTAAACTCCTTTTCTTAGGAAAGAATTATGAC

-continued

GGTACCTAAGGAATAAGCACCGGCTAACTCCGTGCCAGCAGCCGCGGTAA

TACGGGGGGTGCAAGCGTTACTCGGAATCACTGGGCGTAAAGGACGCGTA

GGCGGATTATCAAGTCTCTTGTGAAATTTAACGGCTTAACCGTTAAACTG

CTTGGGAAACTGATAATCTAGAGTAAGGGAGAGGCAGATGGAATTCTTGG

TGTAGGGGTAAAATCCGTAGAGATCAAGAAGAATACTTATTGCGAAGGCG

ATCTGCTAGAACTTAACTGACGCTAATGCGTGAAAGCGTGGGGAGCAAAC

Other representative sequences of this genus will be known by the person skilled in the art and they will serve to identify those bacteria belonging to this genus in a saliva or breath sample.

Additionally, it is noted that, in the context of the present invention, the *Rothia* genus is at increased levels in salivary biological samples of patients with epidermoid cancer of the head and neck compared with general population. Furthermore, it is noted that the following sequences SEQ ID NO 10 to SEQ ID NO 12, are representative sequences of this genus and, therefore, useful for identification of bacteria belonging to this genus in such samples through PCR or any other sequencing technique, including the molecular diagnostic techniques used by DNA microarray.

SEQ ID NO 10

>efea3bb92600988408d794a5d199c1f3
GGGAATCTTCGGCAATGGACGGAAGTCTGACCGAGCAACGCCGCGTGAGT

GAAGAAGGTTTTCGGATCGTAAAGCTCTGTTAGCAGGGAAGAAGAGAGAT

TGACGGTACCTGCAGAGAAAGCGCCGGCTAACTACGTGCCAGCAGCCGCG

GTAATACGTAGGGCGCGAGCGTTGTCCGGAATTATTGGGCGTAAAGAGCT

TGTAGGCGGTTTGTCGCGTCTGCTGTGAAAGGCCGGAGCTTAACTCCGTG

TATTGCAGTGGGTACGGGCAGACTAGAGTGCAGTAGGGGAGACTGGAACT

CCTGGTGTAGCGGTGGAATGCGCAGATATCAGGAAGAACACCGATGGCGA

AGGCAGGTCTCTGGGCTGTAACTGACGCTGAGAAGCGAAAGCATGGGGAG

CGAAC

SEQ ID NO 11

>8f1f146c86e844fcfd81a5c504efea83
AGGAATATTGGTCAATGGGCGCGAGCCTGAACCAGCCAAGTAGCGTGCAG

GATGACGGCCCTATGGGTTGTAAACCTCTGTTAGCAGGGAAGAAGAGAGA

TTGACGGTACCTGCAGAGAAAGCGCCGGCTAACTACGTGCCAGCAGCCGC

GGTAATACGTAGGGCGCGAGCGTTGTCCGGAATTATTGGGCGTAAAGAGC

TTGTAGGCGGTTTGTCGCGTCTGCTGTGAAAGGCCGGAGCTTAACTCCGT

GTATTGCAGTGGGTACGGGCAGACTAGAGTGCAGTAGGGGAGACTGGAAT

TCCTGGTGTAGCGGTGGAATGCGCAGATATCAGGAGGAACACCGATGGCG

AAGGCAGGTCTCTGGGCTGTAACTGACGCTGAGAAGCGAAAGCATGGGGA

GCGAAC

SEQ ID NO 12

>40a5d7d7947a9b9f428d2a4de54030d2
GGGAATATTGCACAATGGGCGCAAGCCTGATGCAGCGACGCCGCGTGAGG

GATGACGGCCTTCGGGTTGTAAACCTCTGTTAGCAGGGAAGAAGAGAGAT

TGACGGTACCTGCAGAGAAAGCGCCGGCTAACTACGTGCCAGCAGCCGCG

-continued

GTAATACGTAGGGCGCGAGCGTTGTCCGGAATTATTGGGCGTAAAGAGCT

TGTAGGCGGTTTGTCGCGTCTGCTGTGAAAGGCCGGAGCTTAACTCCGTG

TATTGCAGTGGGTACGGGCAGACTAGAGTGCAGTAGGGGAGACTGGAATT

CCTGGTGTAGCGGTGAAATGCGTAGATATTAGGAAGAACACCAGTGGCGA

AGGCGACTTTCTGGACGAAAACTGACGCTGAGGCGCGAAAGCCAGGGGAG

CGAAC

Other representative sequences of this genus will be known by the person skilled in the art and they will serve to identify those bacteria belonging to this genus in a saliva or breath sample.

Furthermore, it is noted that, in the context of the present invention, *Catonella* genus is present at lower levels in salivary biological samples of patients with epidermoid cancer of the head and neck compared with general population. Moreover, it is noted that the following sequences SEQ ID NO 13 to SEQ ID NO 15, are representative sequences of this genus and, therefore, useful for identification of bacteria belonging to this genus in such samples through PCR or any other sequencing technique, including the molecular diagnostic techniques used by DNA microarray.

SEQ ID NO 13
>b91a78471249bb403f13253808314b44
GGGGATATTGCACAATGGAGGAAACTCTGATGCAGCGACGCCGCGTGAGT

GAAGAAGTGCTCCGGCATGTAAAGCTCTTTCAGCAGGGAAGATGATGACG

GTACCTGAATAAGAAGCCCCGGCTAACTACGTGCCAGCAGCCGCGGTAAT

ACGTAGGGGGCAAGCGTTATCCGGATTTACTGGGTGTAAAGGGAGCGCAG

GCGGTCTGGCAAGTTGAGAGTGGAAGCAGGGGGCTCAACCCCCTGACTGC

TCCCAAAACTGTTGGACTGGAGTATGGGAGAGGCAGGCGGAATTCCTAGT

GTAGCGGTGAAATGCTCAGATATTAGGAAGAACACCGGTGGCGAAGGCGG

CCTGCTGGACCAAAACTGACGCTGAGGCTCGAGAGCGTGGGGAGCGAAC

SEQ ID NO 14
>60000a298e962dd45ea8f64f83d13296
GGGGATATTGCACAATGGAGGAAACTCTGATGCAGCGACGCCGCGTGAGT

GAAGAAGTATTTCGGTATGTAAAGCTCTATCAGCAGGGAAGATGATGACG

GTACCTGACTAAGAAGCCCCGGCTAACTACGTGCCAGCAGCCGCGGTAAT

ACGTAGGGGGCAAGCGTTATCCGGATTTACTGGGTGTAAAGGGAGCGCAG

GCGGTTTTGCAAGTTGAGAGTGGAAGCAGGGGGCTCAACCCCTTGACTGC

TCCCAAAACTGTAAAACTTGAGTGTAGATGAGGTAGGCGGAATGCGTGGT

GTAGCGGTGGAATGCATAGATATCACGCAGAACTCCGATTGCGAAGGCAG

CTTACTAAGGTACAACTGACGCTGAAGCACGAAAGCGTGGGTATCAAAC

SEQ ID NO 15
>8a4f390e5a28fa4b319a417165699560
GGGGATATTGCACAATGGAGGAAACTCTGATGCAGCGACGCCGCGTGAGT

GAAGAAGTATTTCGGTATGTAAAGCTCTATCAGCAGGGAAGATGATGACG

GTACCTGACTAAGAAGCCCCGGCTAACTACGTGCCAGCAGCCGCGGTAAT

ACGTAGGGGGCAAGCGTTATCCGGATTTACTGGGTGTAAAGGGAGCGCAG

GCGGTTTTGCAAGTTGAGAGTGGAAGCAGGGGGCTCAACCCCCTGACTGC

-continued

TCCCAAAACTGTAAAACTTGAGTATGGGAGAGGCAGGCGGAATTCCTAGT

GTAGCGGTGAAATGCTTAGATATTAGGAAGAACACCGGTGGCGAAGGCGG

CCTGCTGGACCAAAACTGACGCTGAGGCTCGAAAGCGTGGGTAGCAAAC

Moreover, it is noted that, in the context of the present invention, the *Porphyromona* genus is present at lower levels in salivary biological samples of patients with epidermoid cancer of the head and neck compared with general population. Furthermore, it is noted that the following sequences SEQ ID NO 16 to SEQ ID NO 18, are representative sequences of this genus and, therefore, useful for identification of bacteria belonging to this genus in such samples through PCR or any other sequencing technique, including the molecular diagnostic techniques used by DNA microarray.

SEQ ID NO 16
>70a4cb1a6aa33f9abfdf84f2c9707e1b
AGGAATATTGGTCAATGGGCGAGAGCCTGAACCAGCCAAGTCGCGTGAAG

GATGACTGTCTTATGGATTGTAAACTTCTTTTATACGGGAATAACAAGAG

CCACGTGTGGCTCCCTGCATGTACCGTATGAATAAGCATCGGCTAACTCC

GTGCCAGCAGCCGCGGTAATACGGAGGATGCGAGCGTTATCCGGATTTAT

TGGGTTTAAAGGGTGCGTAGGCGGCCTGTTAAGTAAGTGGTTAAATTGTT

GGGCTCAACCCAATCCAGCCACTTAAACTGGCAGGCTAGAGTATTGGAGA

GGCAAGTGGAATTCCATGTGTAGCGGTAAAATGCGTAGATATATGGAGGA

ATACCGATGGCGAAGGCAGCCTCCTGGGATAACACTGACGTTCATGCTCG

AAAGCGTGGGTAGCAAAC

SEQ ID NO 17
>a37c30c91c4a20d9074d2eb6757a8ef8
AGGAATCTTCCACAATGGGCGAAAGCCTGATGGAGCAACGCCGCGTGAAG

GATGAAGGCCTTCGGGTTGTAAACTTCTTTTGTAGGGGAATAAAGAATGG

TACGTGTACCATAGTGAATGTACCCTACGAATAAGCATCGGCTAACTCCG

TGCCAGCAGCCGCGGTAATACGGAGGATGCGAGCGTTATCCGGATTTATT

GGGTTTAAAGGGTGCGTAGGCGGCCTGTTAAGTCAGCGGTGAAATCTAGG

GGCTTAACTCCTAAATTGCCATTGATACTGGTGGGCTTGAGTGTAGATGA

GGTAGGCGGAATGCGTGGTGTAGCGGTGGAATGCATAGATATCACGCAGA

ACTCCAATTGCGAAGGCAGCTTACTAAGGTACAACTGACGCTGAAGCACG

AAAGCGTGGGTATCAAAC

SEQ ID NO 18
>b79c9d865f361911a29c5ccda8af5804
GGGAATATTGCACAATGGGGGAAACCCTGATGCAGCGACGCCGCGTGAGT

GAAGAAGTATTTCGGTATGTAAAGCTCTATCAGCAGGGAAGATAATGACA

GTACCTGACTAAGAAGCCCCGGCTAACTACGTGCCAGCAGCCGCGGTAAT

ACGGAGGATGCGAGCGTTATCCGGATTTATTGGGTTTAAAGGGTGCGTAG

GCGGCCTGTTAAGTCAGCGGTGAAATCTAGGAGCTTAACTCCTAAATTGC

CATTGATACTGGCGGGCTTGAGTGTAGATGAGGTAGGCGGAATGCGTGGT

GTAGCGGTGGAATGCATAGATATCACGCAGAACTCCGATTGCGAAGGCAG

CTTACTAAGGTACAACTGACGCTGAAGCACGAAAGCGTGGGTATCAAAC

Moreover, it is noted that, in the context of the present invention, the *Fretibacterium* genus is at lower levels in salivary biological samples of patients with epidermoid cancer of the head and neck than in general population. Furthermore, it is noted that the following sequences SEQ ID NO 19 to SEQ ID NO 21, are representative sequences of this genus and, therefore, useful for identification of bacteria belonging to this genus in such samples through PCR or any other sequencing technique, including the molecular diagnostic techniques used by DNA microarray.

SEQ ID NO 19
```
>d97b5732e62c39dd8bebf5a5ad9652f0
GGGAATATTGGGCAATGGGAGGAATCCTGACCCAGCGACGCCGCGTGAAC

GAAGACGGCCTTCGGGTTGTAAAGTTCTTTTATGTGGGAAGAATGAAGTG

ACGGTACCACATGAATAAGCCCCGGCTAACTACGTGCCAGCAGCCGCGGT

AATACGTAGGGGGCGAGCGTTGTCCGGAATTACTGGGCGTAAAGGGCACG

CAGGCTGTGCTTCAAGTCAGCTGTAAAAGGATGCGGCTTAACCGTGTTAT

GCGGCTGAGACTGAGGTGCTGGAGTACCGGAGAGGCAAGTGGAATTCCCA

GTGTAGCGGTGAAATGCGTAGATATTGGGAAGAACATCGGTGGCGAAGGC

GACTTGCTGGACGGTAACTGACGCTGAGGTGCGAAAGCCAGGGTAGCGAA

C
```

SEQ ID NO 20
```
>efbe0d96382930addc15fd966fce61e4
GGGAATATTGGGCAATGGGAGGAATCCTGACCCAGCGACGCCGCGTGAAC

GAAGACGGCCTTCGGGTTGTAAAGTTCTTTTATGTGGGAAGAAGGAAGTG

ACGGTACCACATGAATAAGCCCCGGCTAACTACGTGCCAGCAGCCGCGGT

AATACGTAGGGGGCGAGCGTTGTCCGGAATTACTGGGCGTAAAGGGCACG

CAGGCTGTGCTTCAAGTCAGCTGTAAAAGGATGCGGCTTAACCGTGTTAT

GCGGCTGAGACTGAGGTGCTGGAGTACCGGAGAGGCAAGTGGAATTCCCA

GTGTAGCGGTGAAATGCGTAGATATTGGGAAGAACATCGGTGGCGAAGGC

GACTTGCTGGACGGTAACTGACGCTGAGGTGCGAAAGCCAGGGTAGCGAA

C
```

SEQ ID NO 21
```
>f69168cdcc49ef7e9886e21a801d14bd
GGGAATATTGGGCAATGGGAGGAATCCTGACCCAGCGACGCCGCGTGAAC

GAAGACGGCCTTCGGGTTGTAAAGTTCTTTTATGTGGGAAGAATAAAGTG

ACGGTACCACATGAATAAGCCCCGGCTAACTACGTGCCAGCAGCCGCGGT

AATACGTAGGGGGCGAGCGTTGTCCGGAATTACTGGGCGTAAAGGGCACG

CAGGCTGTGCTTCAAGTCAGCTGTAAAAGGATGCGGCTTAACCGTGTTAT

GCAGTTGAGACTGAGGTGCTGGAGTACCGGAGAGGCAAGTGGAATTCCCA

GTGTAGCGGTGAAATGCGTAGATATTGGGAAGAACATCGGTGGCGAAGGC

GACTTGCTGGACGGTAACTGACGCTGAGGTGCGAAAGCCAGGGTAGCGAA

C
```

Thus, a first aspect of the present invention relates to the in vitro use of the level or concentration of bacteria in a salivary or breath sample, belonging to the genus of *Alloprevotella, Prevotella, Campylobacter, Rothia, Catonella, Porphyromona, Fretibacterium*, or any combination thereof, for the diagnosis of head and neck cancer, esophageal cancer, lung cancer, stomach cancer or carcinomas or epidermoid cancers selected from the list consisting of epidermoid cancer of the esophagus, epidermoid cancer of the lung, epidermoid carcinoma of the stomach, or epidermoid cancer of the head and neck, in a patient, or to obtain useful data that enable such diagnosis. Preferably, bacteria belonging to the *Alloprevotella* genus are *Alloprevotella rava* and/or *Alloprevotella tannerae* species. An alternative embodiment of the first aspect of the invention refers to a method for in vitro diagnosis or collection of useful data to support in such diagnosis, of a subject suspected of resembling head and neck cancer, esophageal cancer, lung cancer, stomach cancer or epidermoid cancers selected from the list consisting of epidermoid cancer of the esophagus, epidermoid cancer of the lung, epidermoid carcinoma of the stomach, or epidermoid cancer of the head and neck, which comprises the use as an indicator in a salivary or breath sample obtained from such subject, of the bacteria level or concentration in such sample belonging to the genus of *Alloprevotella, Prevotella, Campylobacter, Rothia, Catonella, Porphyromona, Fretibacterium*, or any combination thereof, where if the level or concentration in such salivary sample of bacteria belonging to the genus of *Alloprevotella, Prevotella, Campylobacter, Rothia, Catonella, Porphyromona, Fretibacterium*, or any combination thereof, differs or varies compared with a salivary or breath sample obtained from a healthy subject or a reference value, this is indicative of a subject with head and neck cancer, esophageal cancer, lung cancer, stomach cancer or carcinomas or epidermoid cancers selected from the list consisting of epidermoid cancer of the esophagus, epidermoid cancer of the lung, epidermoid cancer of the stomach, or epidermoid cancer of the head and neck.

In another preferred embodiment of the first aspect of the invention, the method comprises the use as an indicator in a salivary or breath sample obtained from such subject, of at least the level or concentration in such sample of bacteria belonging to the genus of *Alloprevotella*, where if the level or concentration in the salivary sample of bacteria belonging to such genus is decreased or significantly lower than in a salivary sample obtained from a healthy subject or compared with a reference value, this is indicative of that such subject shows head and neck cancer, esophageal cancer, lung cancer, stomach cancer or carcinomas or epidermoid cancers selected from the list that consists of epidermoid cancer of the esophagus, epidermoid cancer of the lung, epidermoid cancer of the stomach, or epidermoid cancer of the head and neck.

In another preferred embodiment of the first aspect of the invention, the method comprises the use as an indicator in a salivary or breath sample obtained from such subject, of at least the level or concentration in such sample of bacteria belonging to the genus of *Prevotella*, where if the level or concentration in such salivary sample of bacteria belonging to such genus, is decreased or significantly lower than in a salivary or breath sample obtained from a healthy subject or compared with a reference value, this is indicative of that such subject shows head and neck cancer, esophageal cancer, lung cancer, stomach cancer or carcinomas or epidermoid cancers selected from the list that consists of epidermoid cancer of the esophagus, epidermoid cancer of the lung, epidermoid cancer of the stomach, or epidermoid cancer of the head and neck.

In another preferred embodiment of the first aspect of the invention, the method comprises the use as an indicator in a salivary or breath sample obtained from such subject, of at least the level or concentration in such sample of bacteria belonging to the genus of *Campylobacter*, where if the level or concentration in such salivary or breath sample of bacteria belonging to such genus, is decreased or significantly lower than in a salivary or breath sample obtained from a healthy subject or compared with a reference value, this is indicative of that such subject shows head and neck cancer, esophageal cancer, lung cancer, stomach cancer or carcinomas or epidermoid cancers selected from the list consisting of epidermoid cancer of the esophagus, epidermoid cancer of the lung, epidermoid cancer of the stomach, or epidermoid cancer of the head and neck.

In another preferred embodiment of the first aspect of the invention, the method comprises the use as an indicator in a salivary or breath sample obtained from such subject, of at least the level or concentration in such sample of bacteria belonging to the genus of *Catonella*, where if the level or concentration in such salivary or breath sample of bacteria belonging to such genus, is decreased or significantly lower than in a salivary or breath sample obtained from a healthy subject or compared with a reference value, this is indicative of that such subject shows head and neck cancer, esophageal cancer, lung cancer, stomach cancer or carcinomas or epidermoid cancers selected from the list consisting of epidermoid cancer of the esophagus, epidermoid cancer of the lung, epidermoid cancer of the stomach, or epidermoid cancer of the head and neck.

In another preferred embodiment of the first aspect of the invention, the method comprises the use as an indicator in a salivary or breath sample obtained from such subject, of at least the level or concentration in such sample of bacteria belonging to the genus of *Porphyromona*, where if the level or concentration in such salivary or breath sample of bacteria belonging to such genus, is decreased or significantly lower than in a salivary or breath sample obtained from a healthy subject or compared with a reference value, this is indicative of that such subject shows head and neck cancer, esophageal cancer, lung cancer, stomach cancer or carcinomas or epidermoid cancers selected from the list consisting of epidermoid cancer of the esophagus, epidermoid cancer of the lung, epidermoid cancer of the stomach, or epidermoid cancer of the head and neck.

In another preferred embodiment of the first aspect of the invention, the method comprises the use as an indicator in a salivary or breath sample obtained from such subject, of at least the level or concentration in such sample of bacteria belonging to the genus of *Fretibacterium*, where if the level or concentration in such salivary or breath sample of bacteria belonging to such genus, is decreased or significantly lower than in a salivary or breath sample obtained from a healthy subject or compared with a reference value, this is indicative of that such subject shows head and neck cancer, esophageal cancer, lung cancer, stomach cancer or carcinomas or epidermoid cancers selected from the list consisting of epidermoid cancer of the esophagus, epidermoid cancer of the lung, epidermoid cancer of the stomach, or epidermoid cancer of the head and neck.

In another preferred embodiment of the first aspect of the invention, the method comprises the use as an indicator in a salivary or breath sample obtained from such subject, of at least the level or concentration in such sample of bacteria belonging to the genus of Rothia, where if the level or concentration in such salivary or breath sample of bacteria belonging to such genus, is decreased or significantly lower than in a salivary or breath sample obtained from a healthy subject or compared with a reference value, this is indicative of that such subject shows head and neck cancer, esophageal cancer, lung cancer, or stomach cancer or carcinomas or epidermoid cancers selected from the list consisting of epidermoid cancer of the esophagus, epidermoid cancer of the lung, epidermoid cancer of the stomach, or epidermoid cancer of the head and neck.

In the context of the present invention, the epidermoid cancer of the head and neck is considered as the set of malignant tumours produced in the mucosa epithelium of the aerodigestive tracts. This type of cancer represents the 90% of the head and neck cancers and according to their characteristics are classified into three groups:

Oral cavity, pharynx and larynx group: including epidermoid carcinomas mainly related to tobacco and alcohol and with a greater or lesser degree of differentiation.

Nostrils-nasosinusal cavities group: including epidermoid cancers produced in the lining epithelium of the nasal and paranasal sinuses.

Nasopharynx group: including epidermoid cancers mainly related to the Epstein-Barr virus (EBV).

In the context of the present invention, the terms of carcinoma or epidermoid cancer are not only related to epidermoid cancer of the head and neck, but also to epidermoid cancer of the esophagus, epidermoid cancer of the lung and/or epidermoid cancer of the stomach. Epidermoid esophageal carcinoma develops in the inner tissue of the esophagus. It usually occurs in the upper and middle part of the esophagus. It is the most common esophageal cancer in the world. Epidermoid cancer of the lung occurs in the lung tissues, usually in the cells covering the respiratory tract (bronchi) that connect the trachea to the lung. This type of cancer represents between 25 and 30% of lung cancers. Epidermoid cancer of the stomach is a gastric epidermoid cancer that originates in the stomach. It is a very rare tumour, but it should be considered as a possibility of a gastric neoplasm. It is usually diagnosed in advanced stages, which gives it a poor prognosis.

It is noted that, the present invention sufficiently describes the representative nucleotide sequences (i.e SEQ ID No. 1 to SEQ No. 21) that allow identifying the presence as well as the concentration of each of the genera mentioned herein in salivary or breath samples.

A second aspect of the present invention relates to an in vitro method for monitoring the evolution of a subject with head and neck cancer, esophageal cancer, lung cancer, gastric cancer or epidermoid cancers selected from the list consisting of epidermoid cancer of the esophagus, epidermoid cancer of the lung, epidermoid cancer of the stomach, or epidermoid cancer of the head and neck, which comprises the following steps:

Determination of the levels or concentration of bacteria belonging to, at least, one of the following bacterial genera: *Alloprevotella, Prevotella, Campylobacter, Rothia, Catonella, Porphyromona, Fretibacterium*, or any combination thereof, in a saliva or breath sample isolated from such subject; and Comparison of the levels or concentration of such bacteria in such salivary or breath sample with the value obtained in a sample of a healthy subject or with a reference value, where if the level or concentration in such salivary or breath sample of bacteria belonging to the genus of *Alloprevotella, Prevotella, Campylobacter, Rothia, Catonella, Porphyromona, Fretibacterium*, or any combination thereof, differs or varies from a salivary or breath sample obtained from a healthy subject or with respect to a reference value, this is indicative of the favorable or unfavorable evolution of the subject.

A third aspect of the present invention relates to an in vitro method for monitoring the evolution of a subject with head and neck cancer, esophageal cancer, lung cancer, stomach cancer or epidermoid cancers selected from the list consist-
ing of epidermoid cancer of the esophagus, epidermoid
cancer of the lung, epidermoid cancer of the stomach, or
epidermoid cancer of the head and neck, which comprises
the following steps:
    Determination of the levels or concentration of bacteria
      belonging to at least one of the following bacterial
      genera: *Alloprevotella, Prevotella, Campylobacter,
      Rothia, Catonella, Porphyromona, Fretibacterium*, or
      any combination thereof, in a saliva or breath sample
      isolated from such subject; and
    Comparison of the levels or concentration of such bacteria
      in such salivary or breath sample with the value
      obtained in a sample of such subject previously
      obtained, where if the level or concentration in such
      salivary or breath sample of bacteria belonging to the
      genus of *Alloprevotella, Prevotella, Campylobacter,
      Rothia, Catonella, Porphyromona, Fretibacterium*, or
      any combination thereof, differs or varies from such
      previously obtained sample, this is indicative of the
      favorable or unfavorable evolution of the subject.
    A fourth aspect of the invention refers to an in vitro
method for predicting the therapeutic response of a patient
diagnosed with head and neck cancer, esophageal cancer,
lung cancer, stomach cancer or epidermoid cancers selected
from the list consisting of epidermoid cancer of the esopha-
gus, epidermoid cancer of the lung, epidermoid cancer of the
stomach, or epidermoid cancer of the head and neck, where
such method comprises the following steps:
    Determination of the levels or concentration of bacteria
      belonging to at least one of the following bacterial
      genera: *Alloprevotella, Prevotella, Campylobacter,
      Rothia, Catonella, Porphyromona, Fretibacterium*, or
      any combination thereof, in a saliva or breath sample
      isolated from such subject; and
    Comparison of the levels or concentration of such bacteria
      in such salivary or breath sample with the value pre-
      viously obtained in a sample of such subject, where if
      the level or concentration in such salivary or breath
      sample of bacteria belonging to the genus of *Allopre-
      votella, Prevotella, Campylobacter, Rothia, Catonella,
      Porphyromona, Fretibacterium*, or any combination
      thereof, differs or varies from the value previously
      obtained in such sample, this is indicative of the
      favorable or unfavorable evolution of the subject.
    A fifth aspect of the invention refers to an in vitro method
for predicting the therapeutic response of a patient diag-
nosed with head and neck cancer, esophageal cancer, lung
cancer, stomach cancer or epidermoid cancers selected from
the list consisting of epidermoid cancer of the esophagus,
epidermoid cancer of the lung, epidermoid cancer of the
stomach, or epidermoid cancer of the head and neck, where
such method comprises the following steps:
    Determination of the levels or concentration of bacteria
      belonging to at least one of the following bacterial
      genera: *Alloprevotella, Prevotella, Campylobacter,
      Rothia, Catonella, Porphyromona, Fretibacterium*, or
      any combination thereof, in a saliva or breath sample
      isolated from such subject; and
    Comparison of the levels or concentration of such bacteria
      in such salivary or breath sample with the value
      obtained in a sample of a healthy subject or with a
      reference value, where if the level or concentration in
      such salivary or breath sample of bacteria belonging to
      the genus of *Alloprevotella, Prevotella, Campylobacter,
      Rothia, Catonella, Porphyromona, Fretibacterium*, or
      any combination thereof, differs or varies from a salivary or breath sample obtained from a healthy subject
or with respect to a reference value, this is indicative of
favorable or unfavourable response to the treatment.
    It is noted that the specific treatment for each type of
cancer will depend on the stage in which the disease is
found. However, the most common general treatment for
this type of pathologies usually is:
    Partial or radical surgery;
    Radiation therapy;
    Neoadjuvant or induction chemotherapy;
    Concomitant chemoradiotherapy;
    Molecular therapies (monoclonal antibodies). Ex:
      Molecular therapies with cetuximab, a monoclonal
      antibody that binds to the EGFR antigen (Epidermal
      Growth Factor Receptor) in epidermoid cancer of the
      head and neck; and
    Immunotherapy
    Additionally, in the context of the present invention, it is
understood that there is a poor or unfavorable evolution of
the subject if the level or concentration in such salivary or
breath sample of bacteria belonging to the genus of *Allo-
prevotella, Prevotella, Campylobacter, Catonella, Porphy-
romona, Fretibacterium*, or any combination thereof, is
diminished or significantly lower than in a salivary or breath
sample obtained from a healthy subject or with respect to a
reference value or with respect to the value previously
obtained in a salivary or breath sample of the same subject.
    Particularly, in the context of the present invention, it is
understood that there is an unfavourable response to the
treatment if the level or concentration in such salivary or
breath sample of bacteria belonging to the genus of *Allo-
prevotella, Prevotella, Campylobacter, Catonella, Porphy-
romona, Fretibacterium*, or any combination thereof, is
diminished or significantly lower than in a salivary or breath
sample obtained from a healthy subject or with respect to a
reference value or with respect to the value previously
obtained in a salivary or breath sample of the same subject.
    Alternatively or additionally, in the context of the present
invention, it is understood that there is a poor evolution or
unfavorable evolution of the subject if the level or concen-
tration in such salivary or breath sample of bacteria belong-
ing to the *Rothia* genus is increased or significantly higher
than in a salivary or breath sample obtained from a healthy
subject or with respect to a reference value or with respect
to the value previously obtained in a salivary or breath
sample of the same subject.
    Alternatively or additionally, in the context of the present
invention, it is understood that there is an unfavorable
response to the treatment of the subject if the level or
concentration in such salivary or breath sample of bacteria
belonging to the *Rothia* genus is increased or significantly
higher than in a salivary or breath sample obtained from a
healthy subject or with respect to a reference value or with
respect to the value previously obtained in a salivary or
breath sample of the same subject.
    Additionally, in the context of the present invention, the
reference value is preferably understood as the result of the
data of a mathematical algorithm that uses the concentration
and/or the total amount of each bacterium belonging to one
or more of the genera proposed in the present invention for
general population or a healthy subject. The best value for
sensitivity and specificity will be proposed automatically
using the algorithm. This algorithm will provide values
together with the proposed one, as well as changing sensi-
tivity and specificity values providing more information to
physicians and allowing them to decide the best test and
cut-off value for each patient or specific situation.

In the context of the present invention, is possible to determine a bacterium belonging to any proposed genera of the salivary or breath sample from such subject, but not limiting to it, through massive sequencing of the saliva or breath genoma obtaining by this way the total number of bacterial sequences in the saliva together with the total number of other bacteria in that saliva sample. Preferably, such determination is performed by PCR or real-time PCR method.

In another preferred embodiment of the first to fifth aspect of the invention or in any of the preferred embodiments of the invention, such bacteria levels or concentration refer to the total amount of bacteria belonging to genus category out of the total bacteria in such sample.

In another preferred embodiment of the first to fifth aspect of the invention or in any of the preferred embodiments of the invention, the levels or concentration of bacteria belonging to the genus of *Alloprevotella, Prevotella, Campylobacter, Catonella, Porphyromona, Fretibacterium*, or any combination thereof, are determined via an amplification reaction of a nucleic acid preparation derived from such sample using a pair of primers able to amplify one or more representative regions of such genera of bacteria.

Furthermore, in another preferred embodiment of the first to fifth aspect of the invention or in any of the preferred embodiments of the invention, the amplification reaction is carried out by a real-time polymerase chain reaction. Preferably, the detection of the amplification product is accomplished through a fluorescent intercalating agent. More preferably, detection of the amplification product/s is performed by means of a labelled probe, wherein preferably the probe comprises at its 5' end a reporter pigment and at its 3' end a "quencher" pigment or silencer or buffer.

In a sixth aspect of the invention, the method for the first to fifth aspect of the invention or any of its embodiments, further comprises the storage of the method results on a data carrier, preferably wherein such data carrier is readable by computer.

In a seventh aspect of the invention, the method of the first to fifth aspect of the invention or any of its embodiments, include at least the implementation of the comparative step and optionally the provision of a result as a consequence of such comparison by a computer program.

An eighth aspect of the invention refers to a kit including one or more primer pairs able to amplify the bacteria belonging to the genus of *Alloprevotella, Prevotella, Campylobacter, Catonella, Porphyromona, Fretibacterium*, or any combination thereof. Preferably, such kit is used to implement a method for the detection of bacteria from a sample of saliva or breath isolated from a human subject, that comprises the following steps:

i) Contacting the sample to be analyzed with a reaction mixture, containing specific primers able to amplify bacteria belonging to the genus of *Alloprevotella, Prevotella, Campylobacter, Catonella, Porphyromona, Fretibacterium*, or any combination thereof, preferably for the production of Multiplex PCR.

ii) Amplification by means of polymerase chain reaction.

iii) Identification of the products formed in the prior step, being such information indicative of the levels or concentration of bacteria belonging to one or more of the genera of *Alloprevotella, Prevotella, Campylobacter, Catonella, Porphyromona, Fretibacterium*, or any combination thereof.

It is noted that the present invention protects the methodology per se abovementioned, as well as its use for the implementation of any of the methodologies described in the first to seventh aspects of the invention. Also, the present invention protects the use of the kit of the eighth aspect of the invention for implementation of the methodology according to any of the first to fifth aspects of the present invention.

In connection with this eighth aspect of the invention, preferably it provides a method for detecting bacteria belonging to *Alloprevotella rava* and/or *Alloprevotella tannerae*. In a particular embodiment of this eighth aspect of the invention, fragments of DNA included or comprised in sequences 1 to 21 are amplified. In another embodiment of this eighth aspect of the invention, amplification products, which allow to identify the different species and bacterial groups are detected using probes. In a more preferred embodiment, these probes have between 15 to 25 nucleotides in length. The primers can be designed by multiple alignment with programs such as CLUSTAL X, which allow the identification of highly conserved regions that serve as a template.

Given the great abundance of PCR inhibitors, such as humic and fulvic acids, heavy metals, heparin, etc. that result in false negatives, and although there are methods that reduce the concentration of these types of molecules, it is recommendable (see J. Hoorfar et al., "Making Internal Amprolization Control Mandatory for Diagnostic PCR" J. of Clinical Microbiology, Dec 2003, pp.5835) PCR tests containing an Internal Amplification Control (IAC). This IAC consist of no more than a fragment of DNA, which is amplified simultaneously together with the target sample, so its absence at the end of the tests is indicative of the presence of factors, that have caused an undesired development of the PCR.

Throughout the description, the term "specific" implies that the primers comprise a nucleotide sequence totally complementary to the genes or gene fragments employed by the present invention.

In summary, the knowledge gained on the composition of the salivary microbiota in patients undergoing treatment along with the development of the diagnostic or prognostic KIT based on this salivary microbiota is of crucial importance, since it would allow the oncology specialist who treats these patients to have data on the probability of a patient showing or not epidermoid cancer of the head and neck in his first visits, in addition to the probability of response to treatment, as well as patient evolution.

The following examples are merely illustrative of the present invention, but they should not be construed as limiting it.

BRIEF DESCRIPTION OF THE FIGURES

FIG. 7. ROC curve (the area under the curve is shown in table 2) for the *Alloprevotella* genus.

EXAMPLE

Materials and Methods

Study Population

Figure 1:
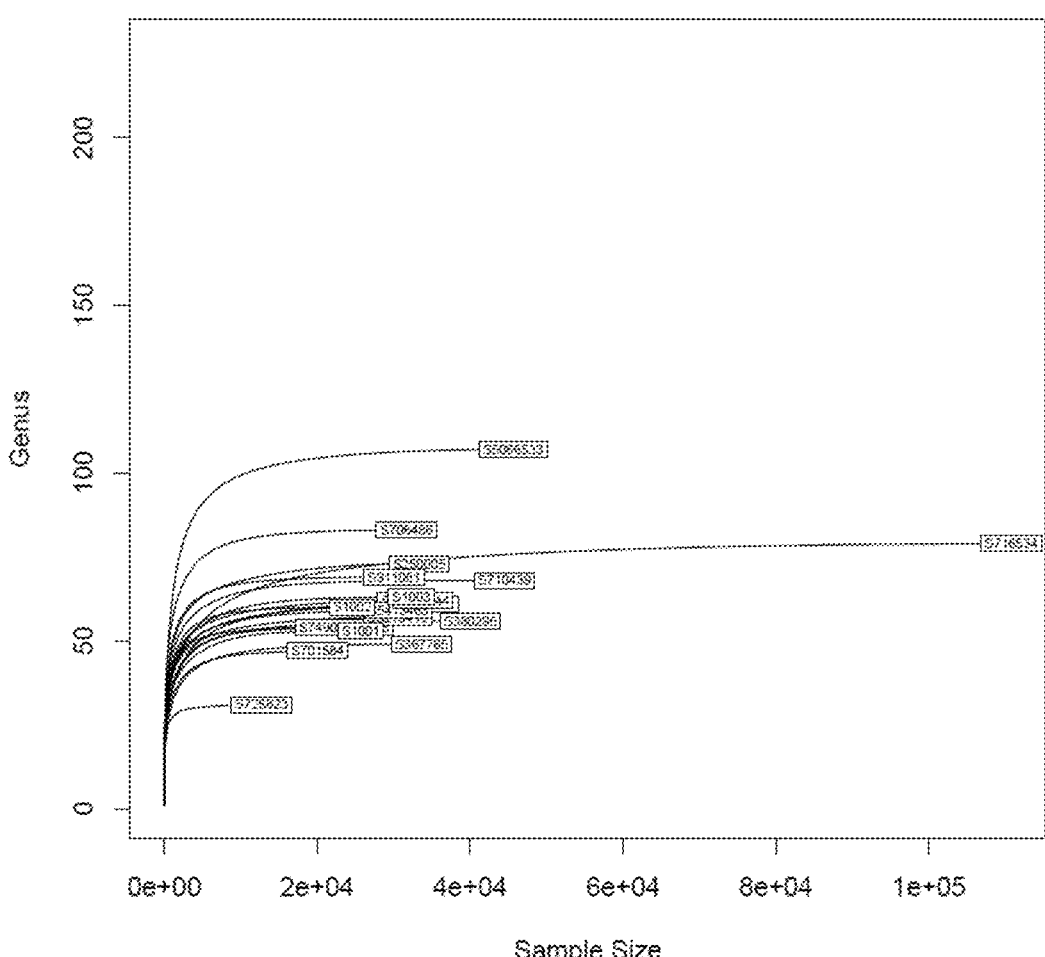
FIG. 1. Rarefaction curves in cases and controls.
Figure 1:
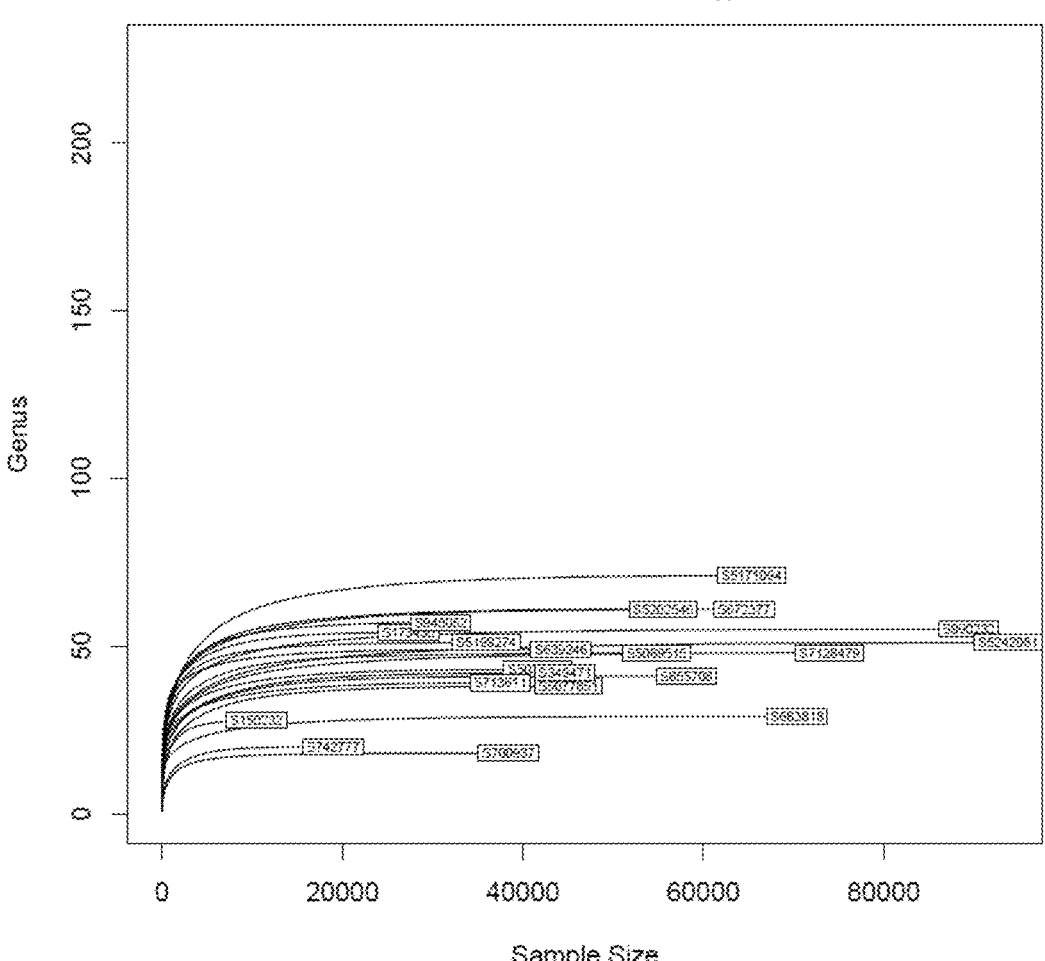
Figure 2:
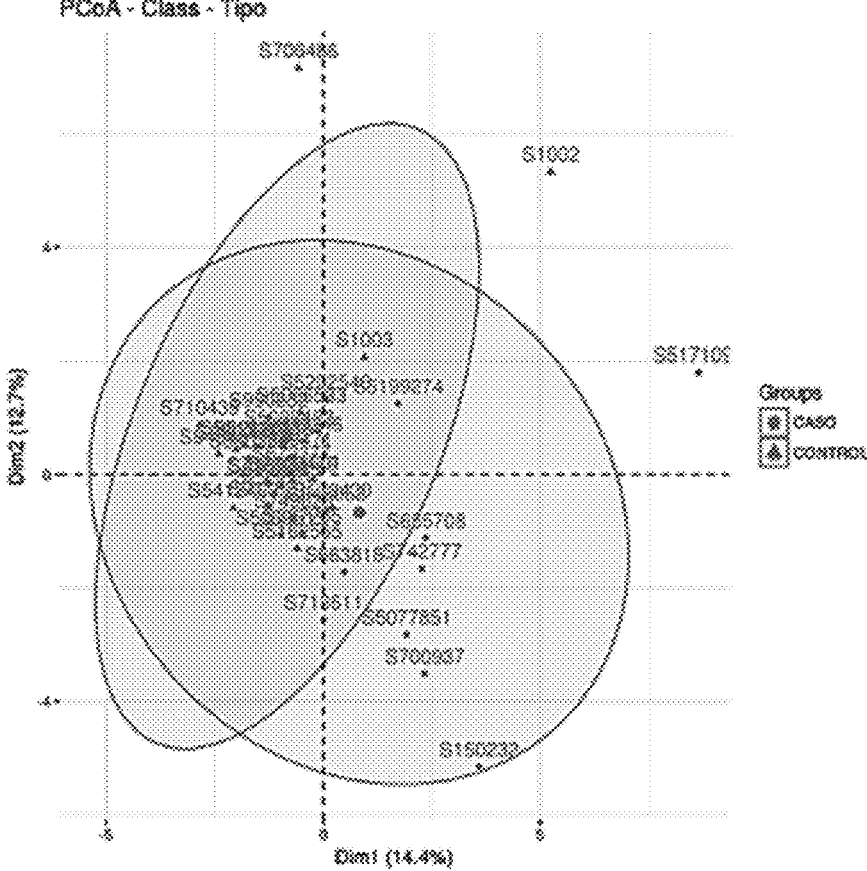
FIG. 2. Analysis of major components in cases and controls.
Figure 3:
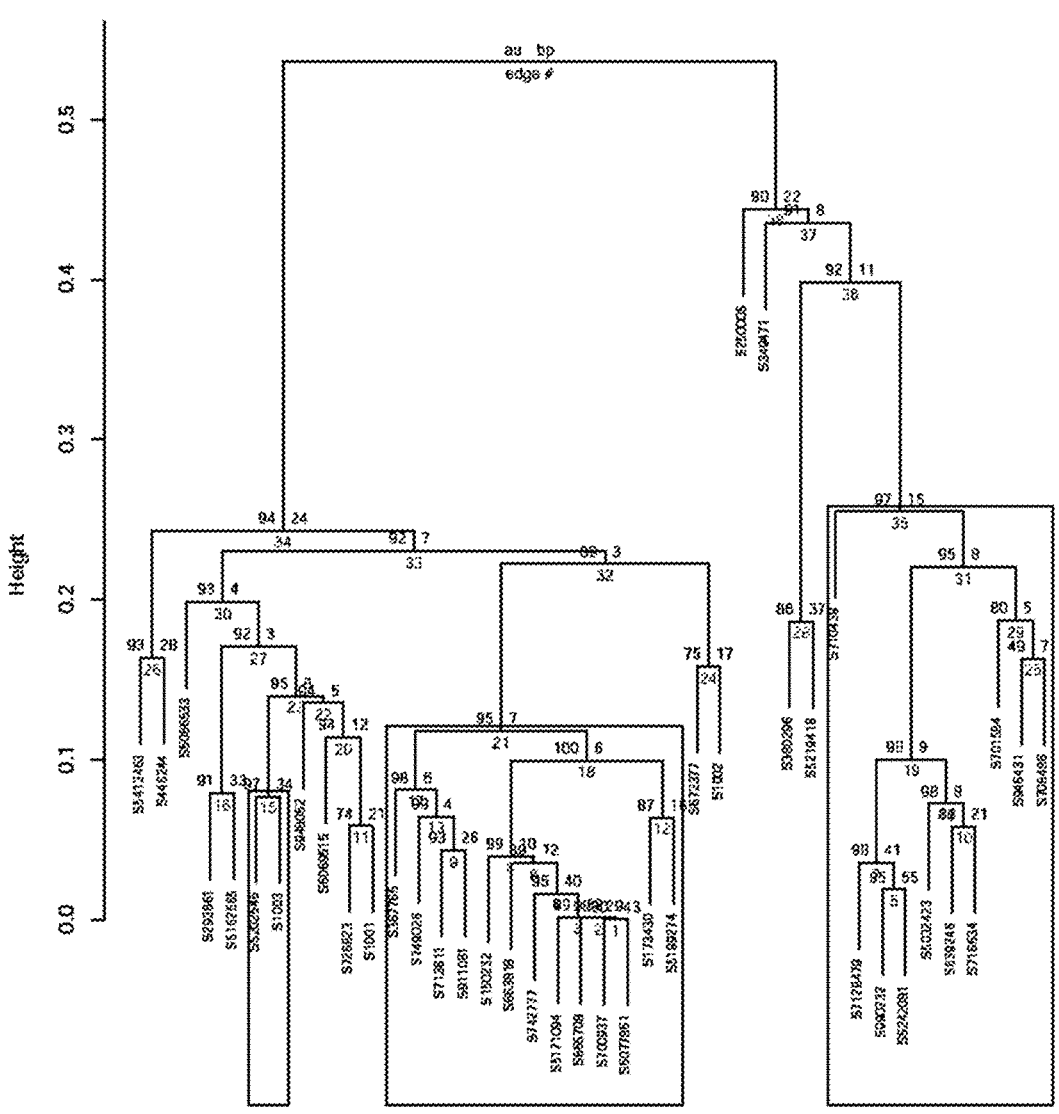
FIG. 3. Clusterization between different microorganisms at the genus level.
Figure 4:
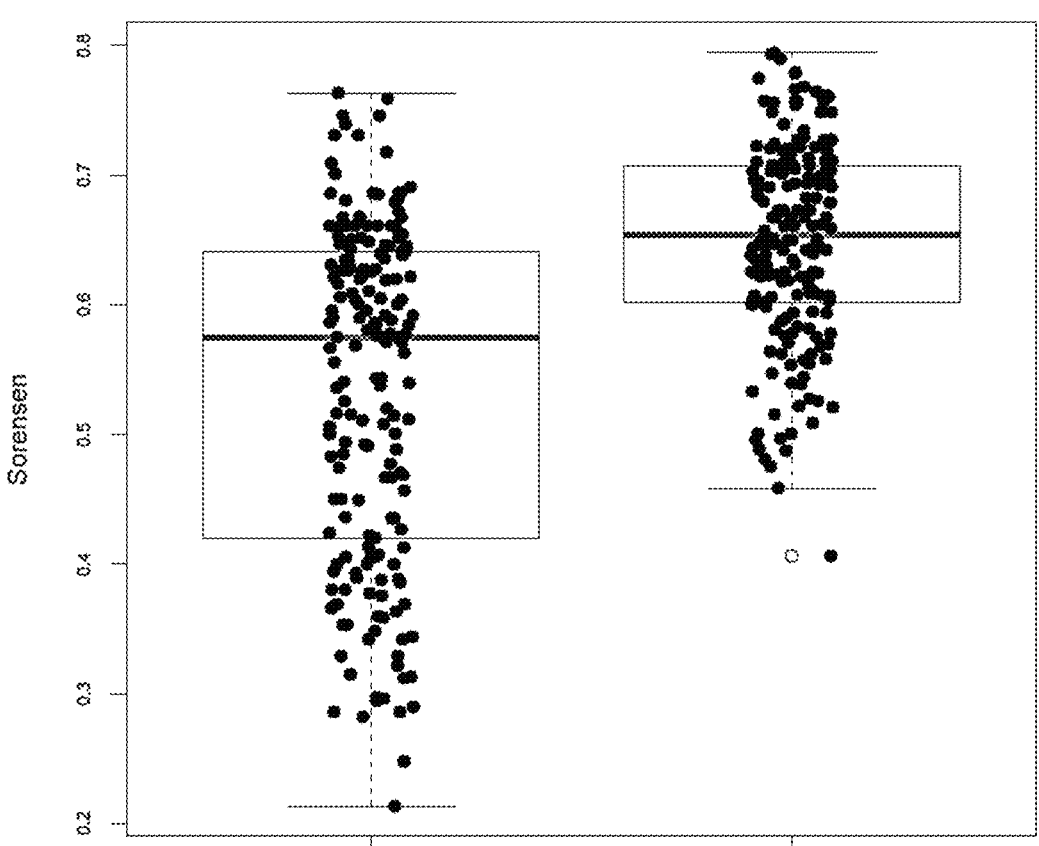
FIG. 4. Beta diversity: genera.
Figure 5:
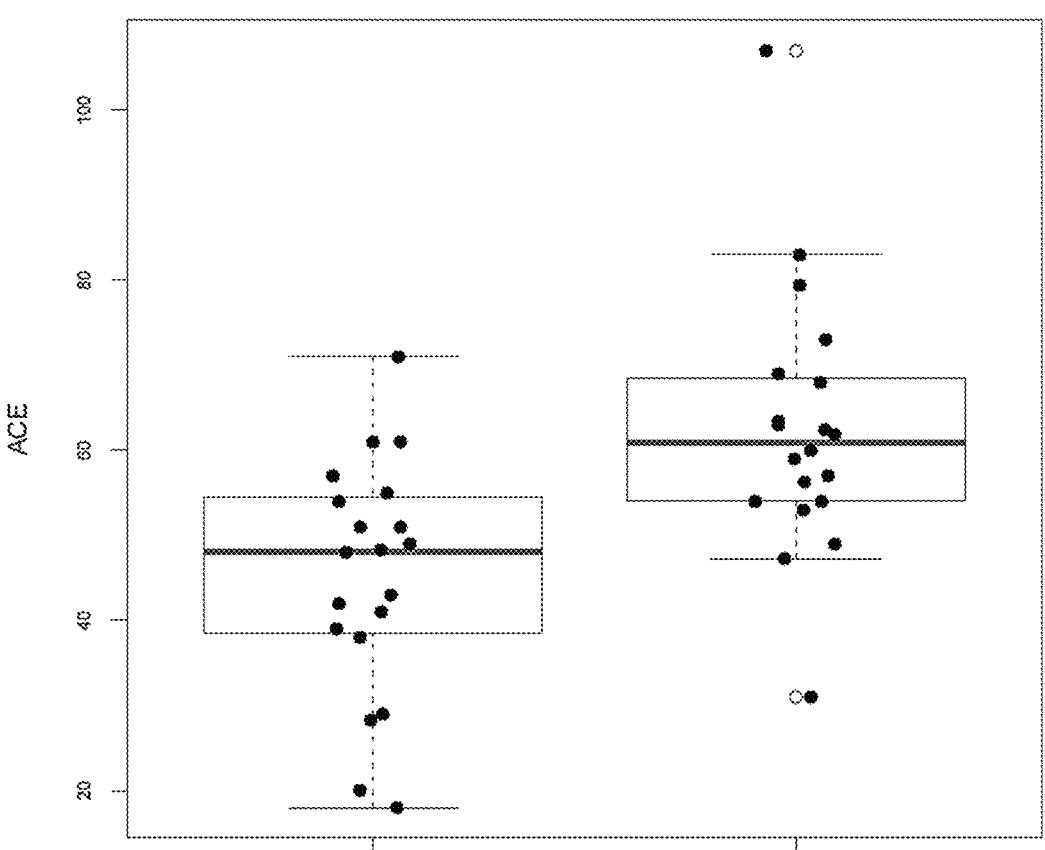
FIG. 5. Alpha diversity: genus.

All patients older than 18 years with an anatomopathological diagnosis of epidermoid carcinoma of pharyngolaryngeal localization were studied.

Samples

Salivary and tissue samples were collected by the Otorhinolaryngology and Molecular Biology service, before signature of the informed consent by all patients who underwent treatment, of benign and malignant head and neck tumours during the period between January 2008 and December 2012, both inclusive. Thereby obtaining an initial total sample of 179 patients.

Subsequently, between these samples a total of 20 patients were chosen and, together with salivary samples from 20 healthy volunteers, an analysis of the hypervariable region of the r516 gene was performed in saliva samples. The results of the sequencing were analyzed in the biomedical research center of Bioithas, located in the scientific park of Alicante. Patients in both groups were selected in order to maintain the homogeneity in their sociodemographic characteristics.

Population included in the final analysis of the data was defined according to the following criteria:

Inclusion Criteria:

18-90 age group.

Location of the original primary tumour in pharynx, larynx or cervical ganglion.

Anatomopathological diagnosis of epidermoid carcinoma.

Curative or palliative surgical treatment.

Collection of biological samples in surgery room: blood, saliva, tumour tissue and healthy tissue.

Exclusion Criteria:

Age less than 18 years or over 90 years.

Primary tumour of localization other than larynx, pharynx and/or lymph nodes.

Anatomopathological diagnosis of benign and malignant tumours of non-epidermoid variants: adenocarcinoma, papillary carcinoma, mucoepidermoid carcinoma, anaplastic carcinoma, melanoma, lymphoepithelioma and paraganglioma.

Treatment with non-surgical organ preservation.

Extranodal metastatic disease concomitant with the primary tumour.

Insufficient tumour samples, with inability for anatomopathological study.

Low number of salivary samples.

Preparation and Collection of Biological Samples

Biological samples were collected in the Otorhinolaryngology operating room at the time prior to the surgical intervention and in a fasting state of patients.

Saliva samples were collected using lentins placed in the sublingual region for a period of 10 minutes and prepared by the researcher. No method was used for the stimulation of salivary production.

All samples were identified and sent to the Research Unit of the Clinical Analysis Service (Laboratory of Molecular Therapy and Cancer Biomarkers), where they were processed. Saliva was centrifuged at 2500 rpm, 5 minutes, the supernatant was aliquotted and frozen at −80° C. until next use.

Statistic Analysis

Contingency tables and "Chi square $(X^2)$" statistical test were used. Comparison of means with a dichotomous variable was evaluated using "Student's t" statistical test, as long as one variable was quantitative and the other categorical. In cases which the qualitative variable had more than 2 categories, the one-way variance analysis (ANOVA) was used.

Different analysis curves were elaborated: ROC curves (acronym of Receiver Operating Characteristic), for the graphic representation of Sensitivity versus 1—Specificity. Optimal cut-off point was determined for each salivary microbiome pattern by searching for the Yoiden index (IY) or maximum sensitivity and specificity point. Area under the curve (AUC) was calculated by the numerical integration of the ROC curves. Concentration with the highest AUC was identified as the strongest predictor for detection of epidermoid cancer of the head and neck. Data were analyzed using SPSS© (version 15.0) software.

Results

During the study period, a total of 20 patients with tumour pathology and 20 healthy patients corresponding to the control group were analyzed. Clinical-pathological characteristics of these patients are summarized in Table 1 below.

TABLE 1

| Clinico-pathological characteristics of the patients under study | |
| --- | --- |
| Feature | No. of cases (%) |
| Age | |
| <55 yo | 8 (10,5) |
| 50-59 yo | 26 (34,2) |
| 60-69 yo | 25 (32,9) |
| 70-79 yo | 12 (15,8) |
| >80 yo | 5 (6,6) |
| Sex | |
| Male | 75 (98,7) |
| Female | 1 (1,3) |
| Tobacco | |
| Yes | 69 (92,0) |
| No | 6 (8,0) |
| Alcohol | |
| Yes | 55 (72,4) |
| No | 21 (27,6) |

TABLE 1-continued

| Clinico-pathological characteristics of the patients under study | |
| --- | --- |
| Feature | No. of cases (%) |
| Comorbidities | |
| Diabetes | 12 (15,8) |
| EPOC | 27 (35,5) |
| Heart disease | 19 (25,0) |
| Liver disease | 6 (7,9) |
| Location | |
| Larynx | 69 (90,8) |
| Supreglottis | 26 (37,1) |
| Glottis | 42 (60,0) |
| Subglottis | 2 (2,9) |
| Pharynx | 7 (9,2) |
| Clasification pT | |
| T1 | 13 (17,8) |
| T2 | 20 (27,4) |
| T3 | 28 (38,4) |
| T4 | 12 (16,4) |
| Clasification pN | |
| N0 | 53 (69,7) |
| N1 | 7 (9,2) |
| N2 | 10 (13,2) |
| N3 | 6 (7,9) |

TABLE 1-continued

| Clinico-pathological characteristics of the patients under study | |
| --- | --- |
| Feature | No. of cases (%) |
| Stages | |
| Stage I | 13 (17,1) |
| Stage II | 20 (26,3) |
| Stage III | 22 (28,9) |
| Stage IV | 21 (27,6) |
| Stage type | |
| Initial | 33 (43,4) |
| Advanced | 43 (56,6) |

Patients range from 38 to 86 years old with an average of 61.9 years old and a predominance of males (98.7%). 92% of the patients had a smoking habit and 72.4% had an enolic one. The majority had tumour of laryngeal location (90.8%), being the most frequent group the one corresponding to glottic tumours (60.0%).

From the obtained salivary samples, those genera with significant differences between groups were analyzed. These results are shown below in table 2.

TABLE 2

| | g__Rothia | g__Porphyromonas | g__Alloprevotella | g__Prevoteila 7 | g__Campylobacter | g__Catonella | g__Fretibacterium |
| --- | --- | --- | --- | --- | --- | --- | --- |
| | Test Statistics[a] | | | | | | |
| Marin-Whitney U | 72,000 | 70,000 | 13,500 | 66,000 | 31,000 | 74,500 | 53,000 |
| Wilcoxon W | 282,000 | 280,000 | 223,500 | 266,000 | 241,000 | 284,500 | 263,000 |
| Z | −3,462 | −4,228 | −5,085 | −4,214 | −4,573 | −3,422 | −4,255 |
| Asym Sig. (2-tailed) | 0.001 | 0.000 | 0.000 | 0.000 | 0.000 | 0.001 | 0.000 |

[a]Grouping Variable: caso 1

Additionally, and on the basis of table 2 and FIGS. 6 to 13, table 3 shows the different areas under the curve for each of the genera showing statistically significant differences between groups in the present study:

TABLE 3

Characteristics of salivary microbiota results obtained from ROC curves.
ROC Area Under the Curve

| Contrast variables | Area | Typical error | Asymptotic significance | Cut-off values | Sensibility | Specificity |
| --- | --- | --- | --- | --- | --- | --- |
| *Prevotella* | 0.86 | | | 8 | 0.65 | 0.95 |
| *Alloprevotella* genus | 0.966 | | | 19 | 0.95 | 0.85 |
| *Alloprevotella* rava | 0.966 | | | 19 | −0.95 | −0.85 |
| *Alloprevotella* Tannarae | 0.966 | | | 19 | −0.95 | −0.85 |
| *Campylobacter* genus | 0.923 | | | 61.5 | 1 | 0.80 |
| *Rothia* genus | 0.820 | | | 9563 | 0.75 | 0.85 |
| *Catonella* genus | 0.814 | | | 54 | 0.85 | 0.75 |
| *Porphyromona* genus | 0.825 | | | 1.5 | 65 | 1 |
| *Fretibacterium* genus | 0.868 | | | 7.5 | 0.80 | 0.85 |

Figure 6:
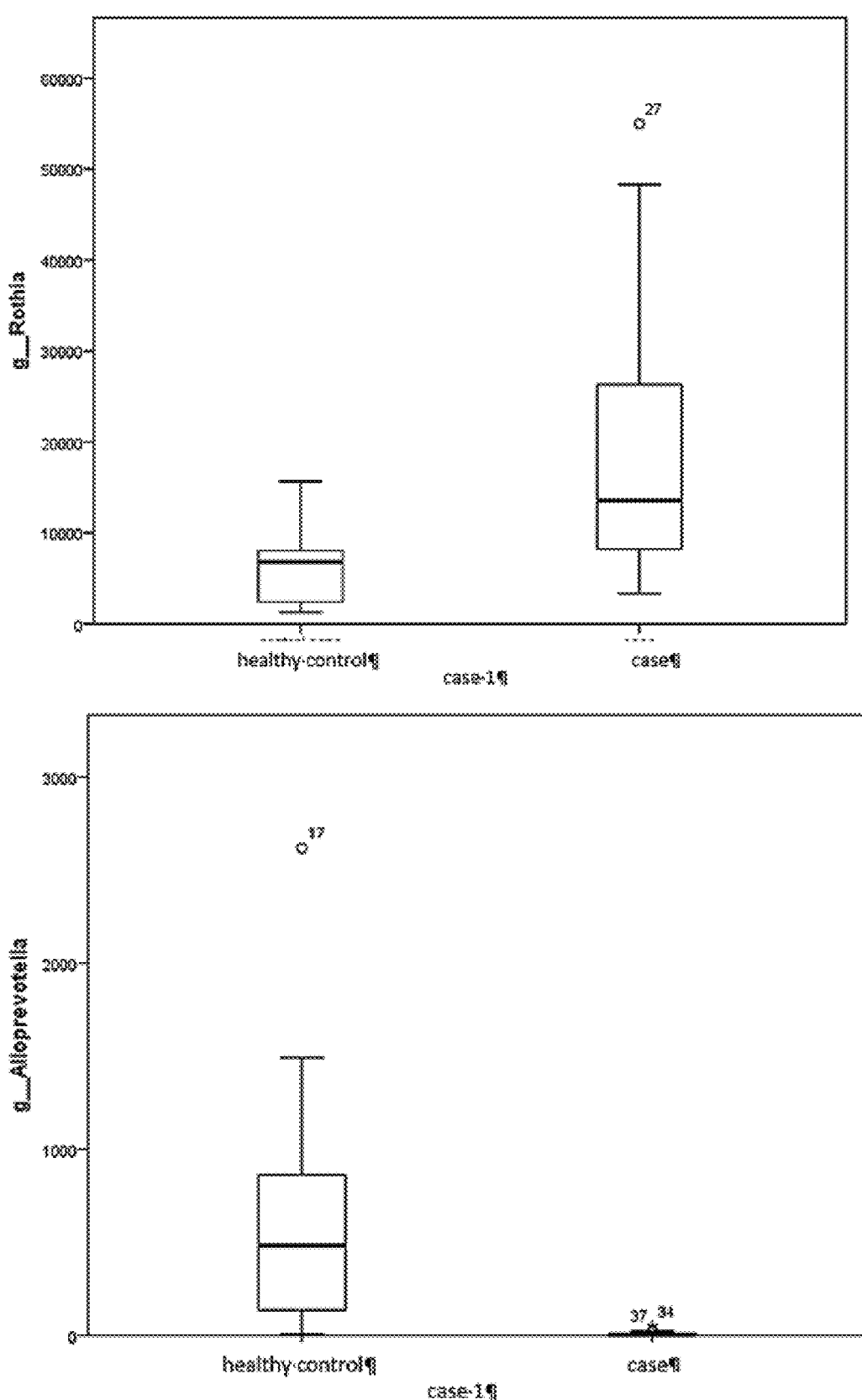
FIG. 6. Differences between groups of genera described in table 2.
Figure 6:
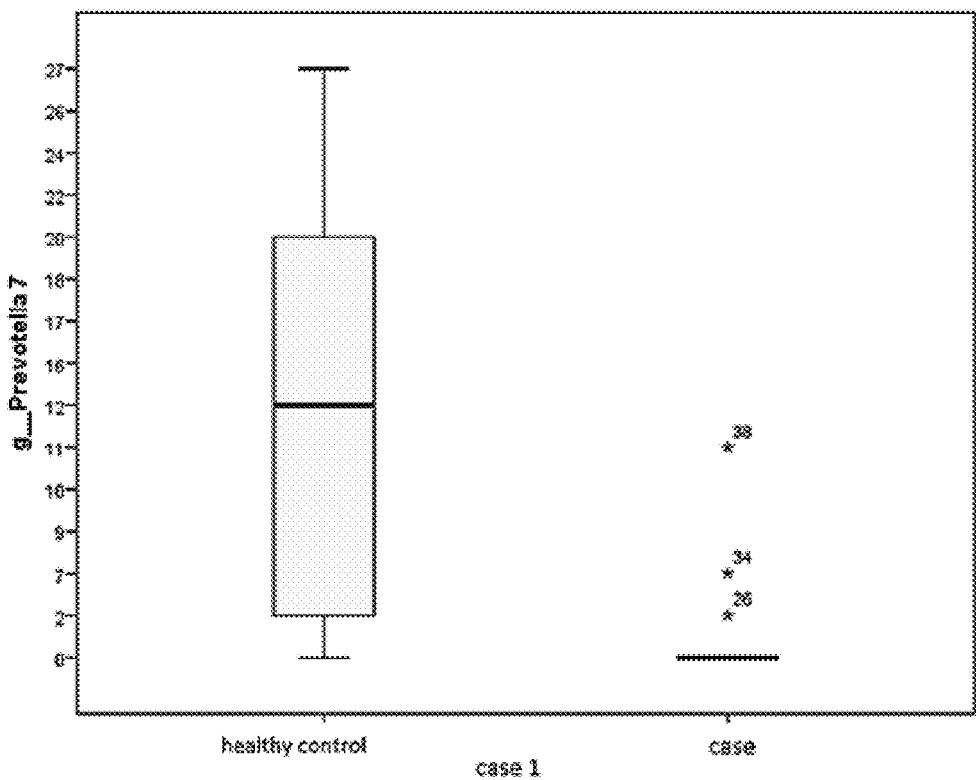
Figure 6:
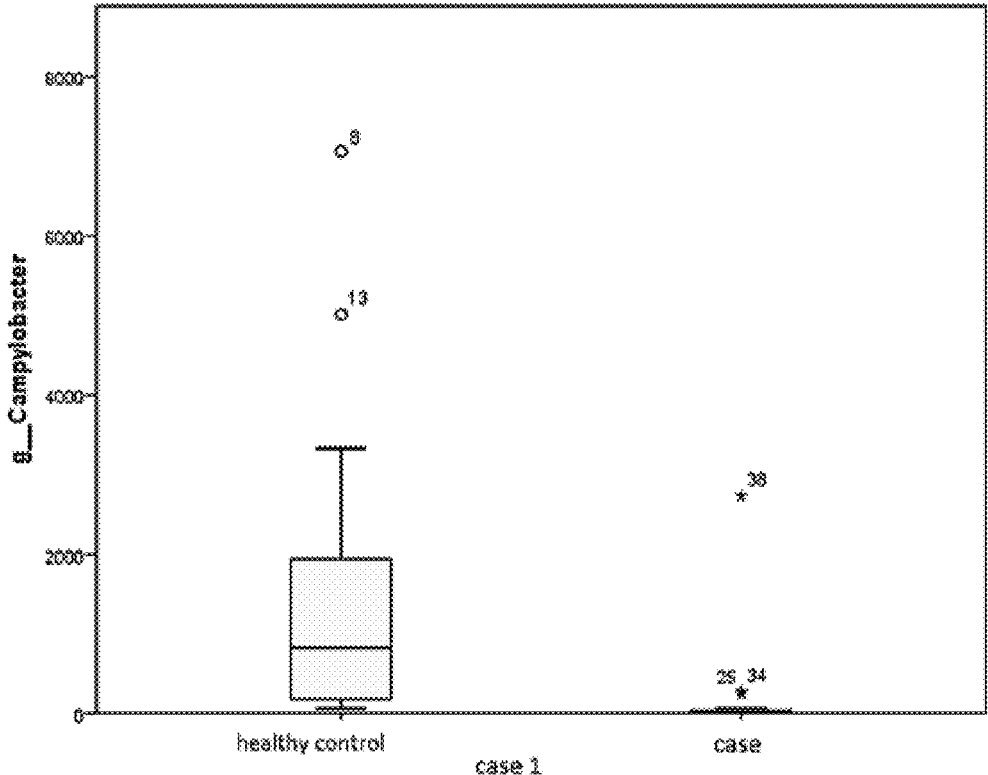
Figure 6:
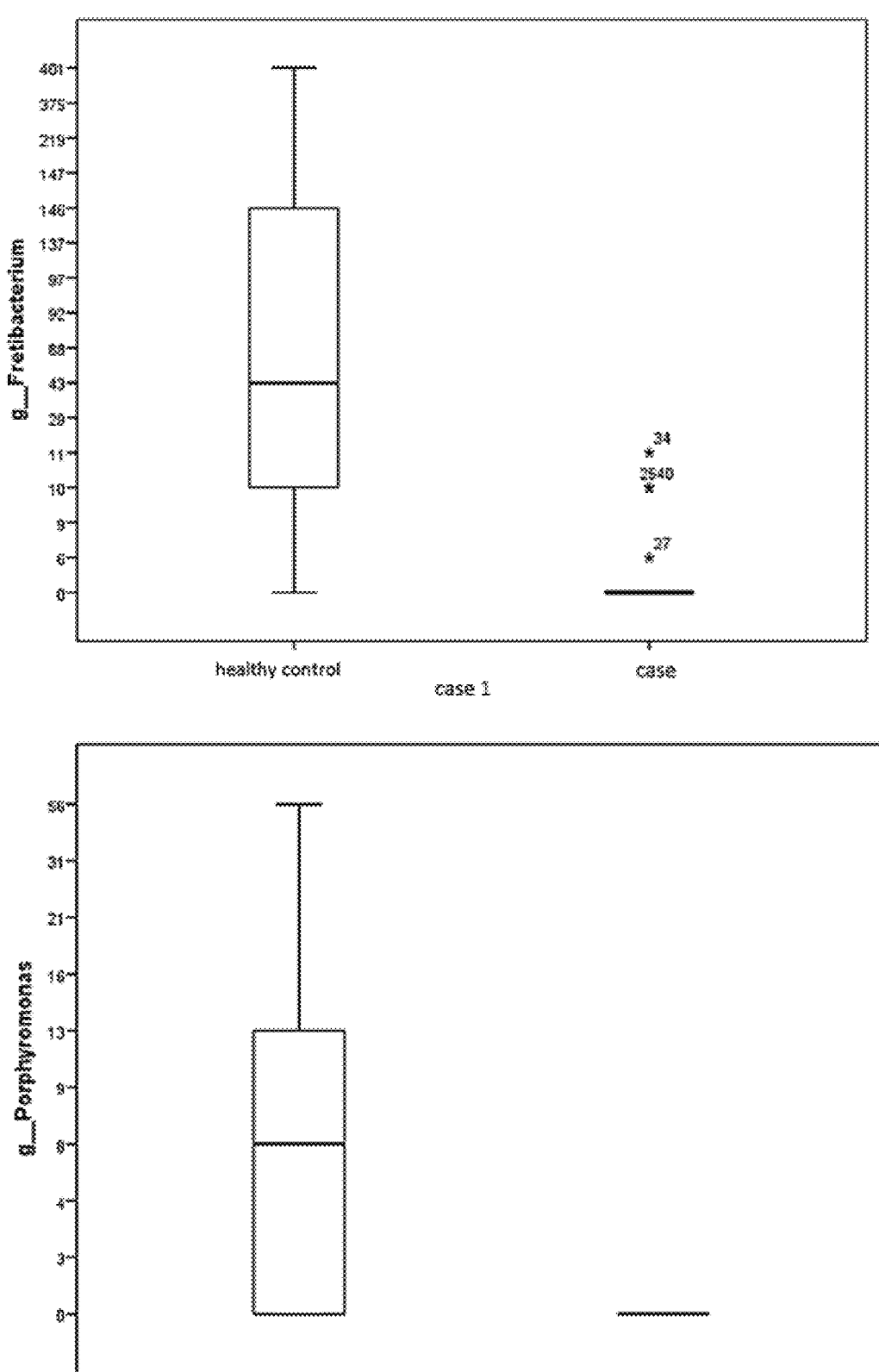
Figure 6:
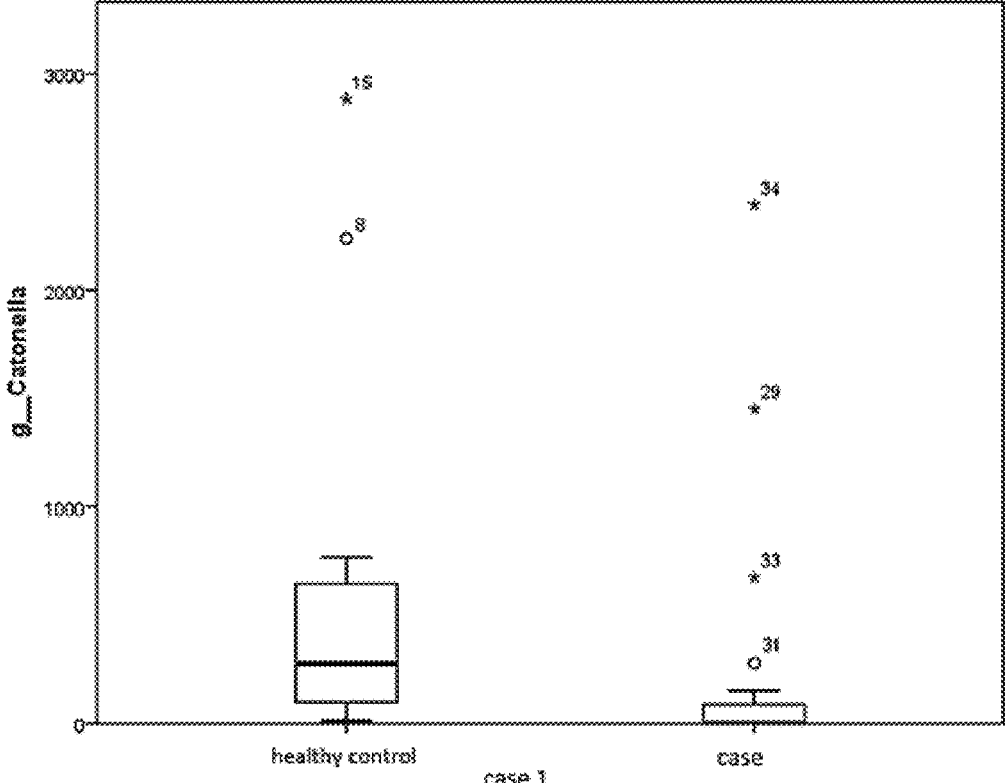
Figure 7:
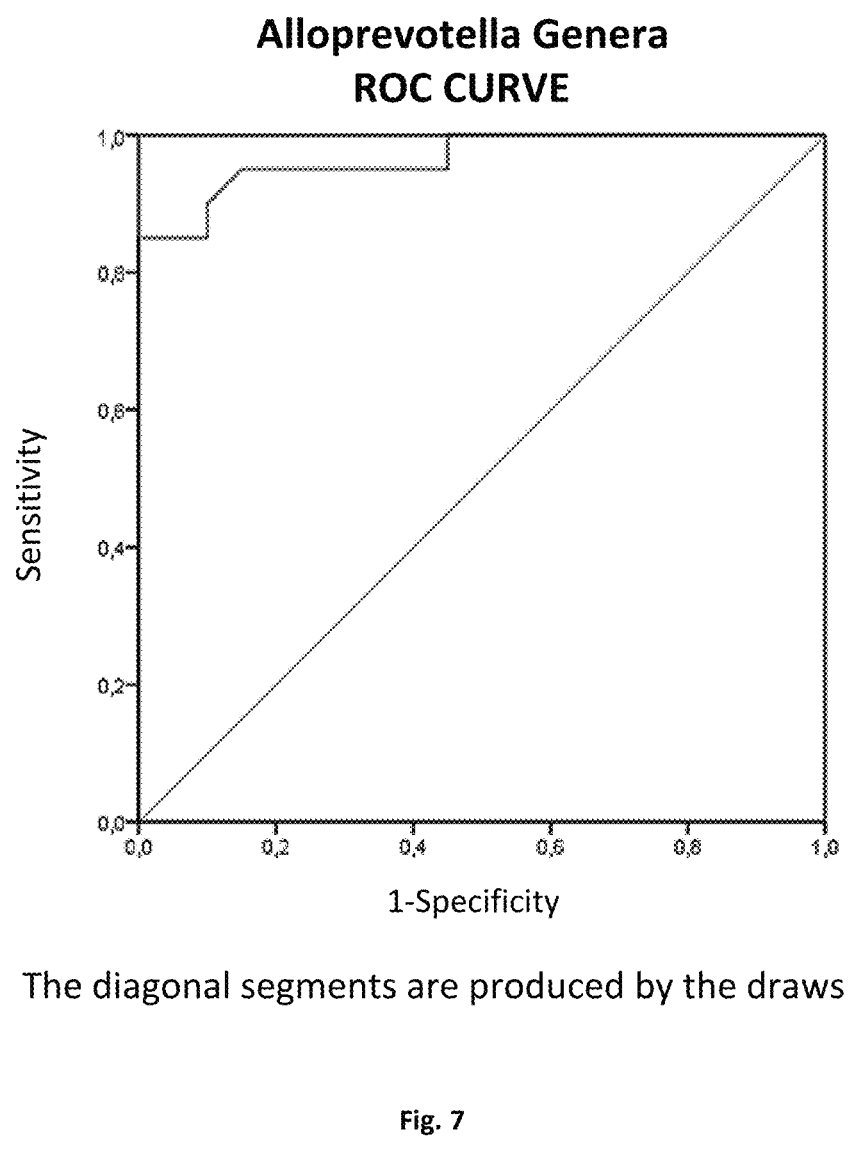

As shown in table 3, FIG. 6 and FIG. 7, both in absolute values and in the presence percentage of *Alloprevotella* genus in salivary samples and, especially, of *Alloprevotella rava* and *Alloprevotella tannera* species, there is a negative correlation between subjects with epidermoid cancer of mouth and pharynx and healthy subjects.

Figure 8:
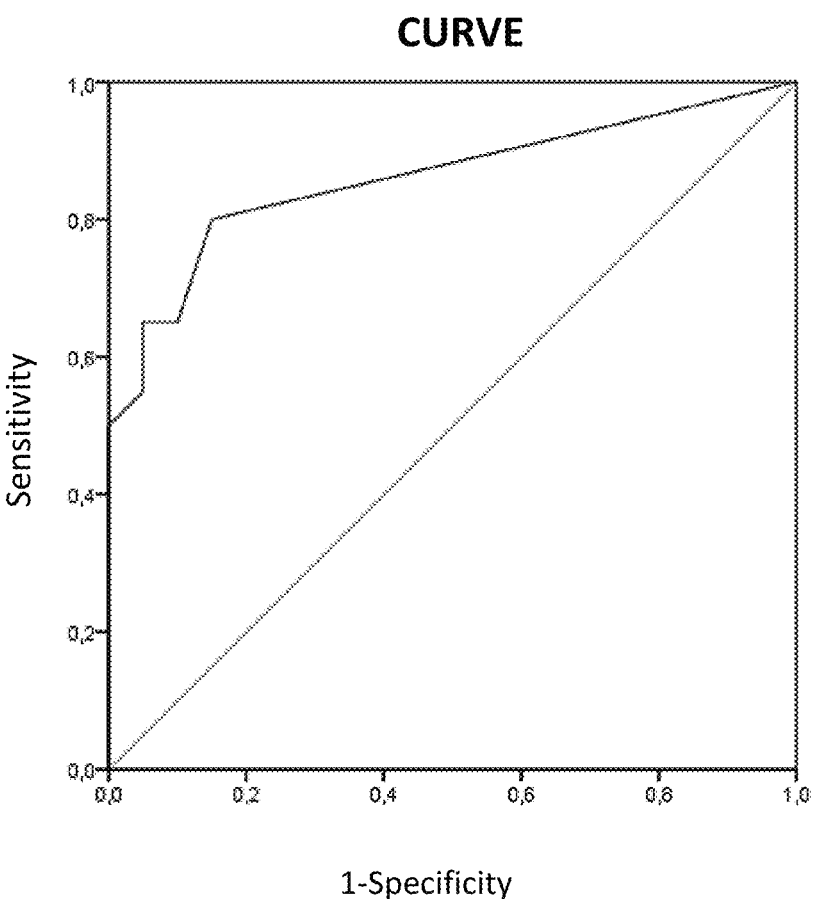
FIG. 8. ROC curve (the area under the curve is shown in table 2) for the *Prevotella* genus.

As shown in table 3, FIG. 6 and FIG. 8, both in absolute values and in the presence percentage of *Prevotella* genus in salivary samples, there is a negative correlation between subjects with epidermoid cancer of the mouth and pharynx and healthy subjects.

Figure 9:
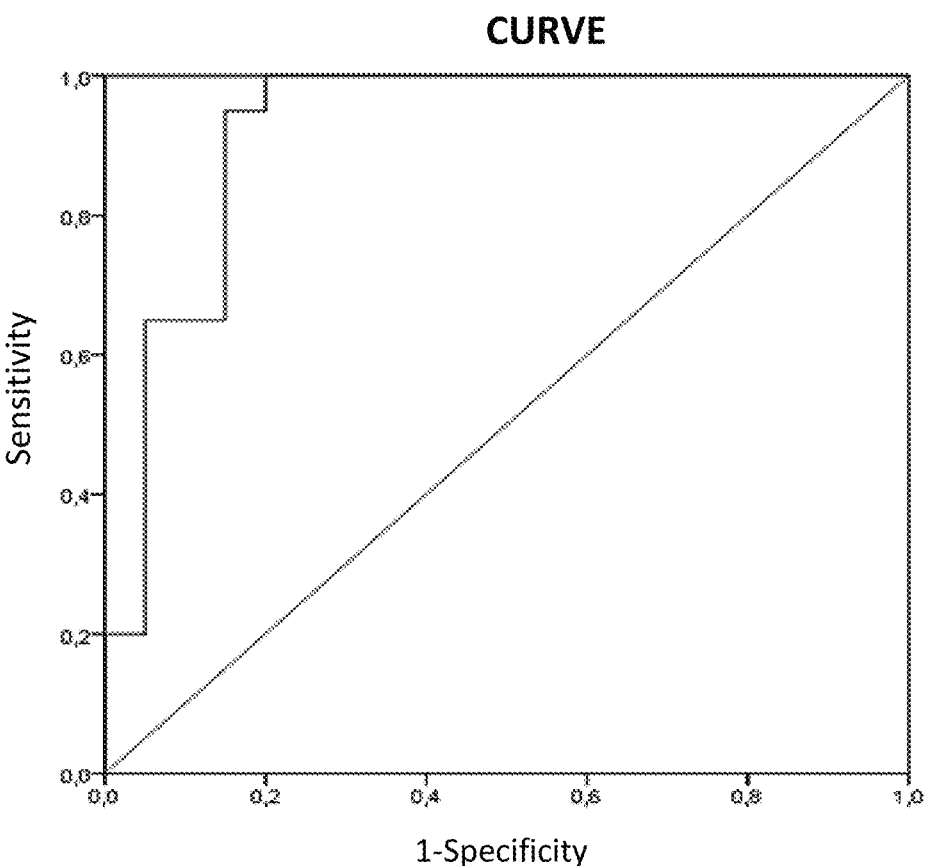
FIG. 9. ROC curve (the area under the curve is shown in table 2) for the *Campylobacter* genus.

As shown in table 3, FIG. 6 and FIG. 9, both in absolute values and in the presence percentage of *Campylobacter* genus in salivary samples, there is a negative correlation between subjects with epidermoid cancer of mouth and pharynx and healthy subjects.

Figure 10:
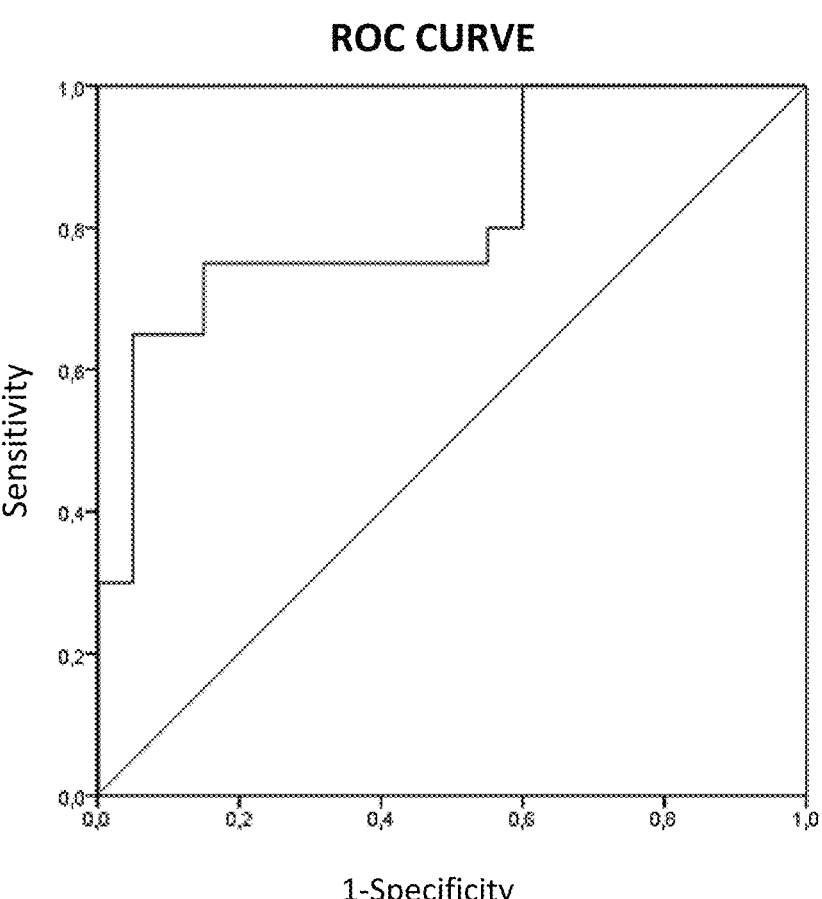
FIG. 10. ROC curve (the area under the curve is shown in table 2) for the *Rothia* genus.

As shown in table 3, FIG. 6 and FIG. 10, both in absolute values and in the presence percentage of *Rothia* genus in salivary samples, there is a positive correlation between subjects with epidermoid cancer of mouth and pharynx and healthy subjects.

Figure 11:
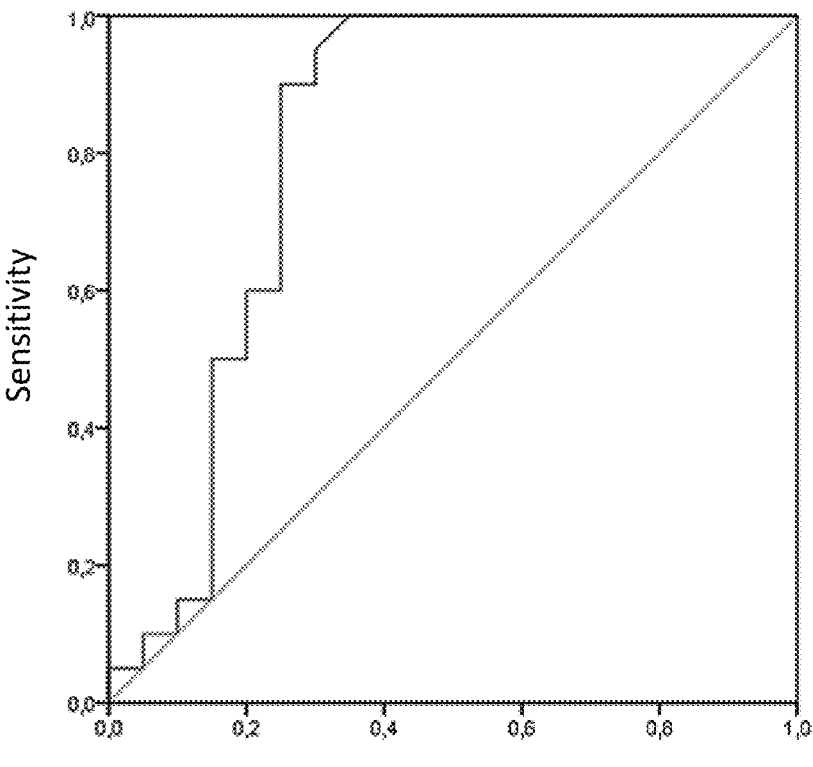
FIG. 11. ROC curve (the area under the curve is shown in table 2) for the *Catonella* genus.

As shown in table 3, FIG. 6 and FIG. 11, both in absolute values and in the presence percentage of *Catonella* genus in salivary samples, there is a negative correlation between subjects with epidermoid cancer of the mouth and pharynx and healthy subjects.

Figure 12:
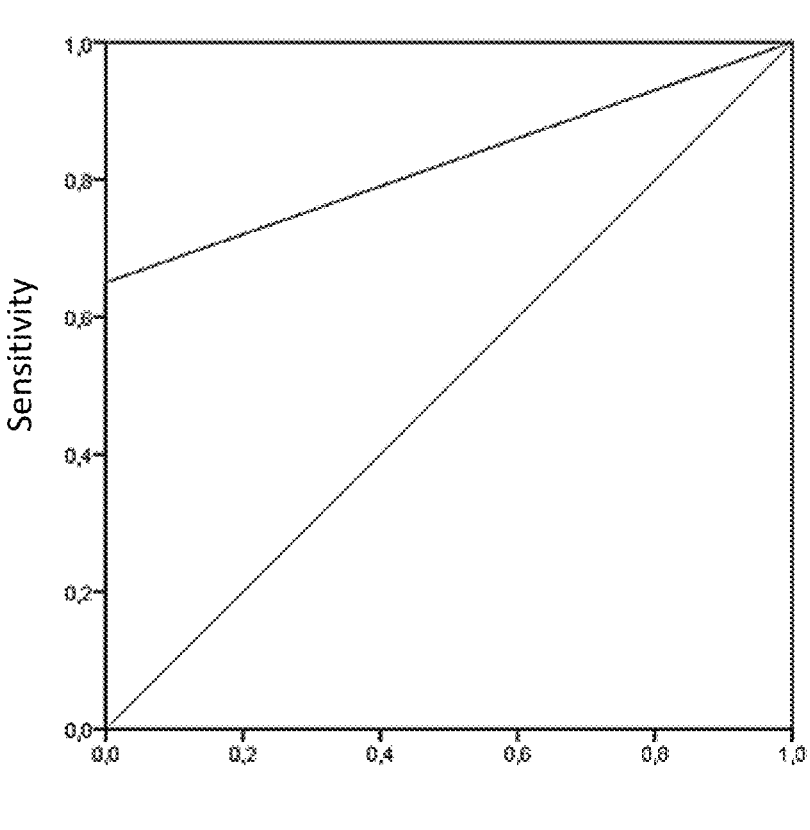
FIG. 12. ROC curve (the area under the curve is shown in table 2) for the *Porphyromonas* genus.

As shown in table 3, FIG. 6 and FIG. 12, both in absolute values and in the presence percentage of *Porphyromona* genus in salivary samples, there is a negative correlation between subjects with epidermoid cancer of the mouth and pharynx and healthy subjects.

Figure 13:
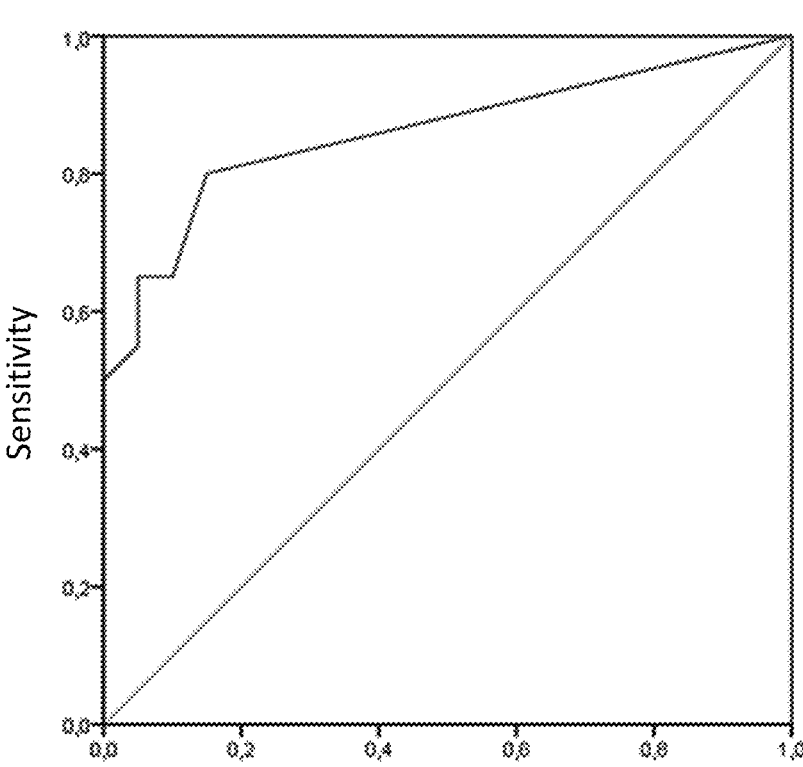
FIG. 13. ROC curve (the area under the curve is shown in table 2) for the *Fretibacterium* genus.

As shown in table 3, FIG. 6 and FIG. 13, both in absolute values and in the presence percentage of *Fretibacterium* genus in salivary samples, there is a negative correlation between subjects with epidermoid cancer of the mouth and pharynx and healthy subjects.

Design of a RNA quantification test (qPCR) by any of the known methods including metagenomics, massive sequencing, qPCR, DNA microarray, and the correlation of these values with the values found by sequencing the hypervariable region Rs16 could be useful for the diagnosis, preferably for the early diagnosis of disease and relapse of epidermoid cancer of the mouth and pharynx.

Additionally, the use of probiotics that modulate the salivary microbiota of these patients could be a preventive or intervention treatment for patients with epidermoid cancer of the larynx and pharynx mouth.

---

The invention claimed is:

1. A method for treating epidermoid cancer of the laryngeal location in a human male patient suspected of having epidermoid cancer of the laryngeal location, comprising:
   i) selecting the patient for treatment when microbiota in a salivary sample of the patient comprises a lower concentration of bacteria belonging to the *Alloprevotella* genus relative to a predetermined reference cut-off value; and
   administering to the—patient a treatment for epidermoid cancer of the laryngeal location, wherein the treatment is selected from the group consisting of a partial or radical surgery, a radiation therapy, a neoadjuvant or induction chemotherapy, a concomitant chemoradiotherapy, a molecular therapy, an immunotherapy and combinations thereof.

2. The method of claim 1, wherein the concentration of bacteria belonging to the *Alloprevotella* genus has been determined according to a method, comprising:
   i) obtaining a salivary sample from the patient;
   ii) contacting bacterial DNA obtained from the sample with reagents and primers for amplifying bacteria belonging to the *Alloprevotella* genus and labelled reagents for detecting DNA belonging to the *Alloprevotella* genus; and
   iii) amplifying the bacterial DNA to form an amplified DNA product comprising DNA of bacteria belonging to the *Alloprevotella* genus and detecting the amplified DNA product.

3. The method of claim 1, wherein the bacteria belonging to the *Alloprevotella* genus is *Alloprevotella* rava species or *Alloprevotella tannerae* species.

4. The method of claim 1, further comprising selecting the patient for treatment when the microbiota in the salivary sample comprise a lower concentration of bacteria belonging to the *Prevotella* genus relative to a predetermined cut-off value.

5. The method of claim 1, further comprising selecting the patient for treatment when the microbiota in the salivary sample comprise a lower concentration of bacteria belonging to the *Campylobacter* genus relative to a predetermined cut-off value.

6. The method of claim 1, further comprising selecting the patient for treatment when the microbiota in the salivary sample comprise a lower concentration of bacteria belonging to the *Catonella* genus relative to a predetermined cut-off value.

7. The method of claim 1, further comprising selecting the patient for treatment when the microbiota in the salivary sample comprise a lower concentration of bacteria belonging to the *Porphyromonas* genus relative to a predetermined cut-off value.

8. The method of claim 1, further comprising selecting the patient for treatment when the microbiota in the salivary sample comprise a lower concentration of bacteria belonging to the *Fretibacterium* genus relative to a predetermined cut-off value.

9. The method of claim 1, further comprising administering a probiotic that modulates salivary microbiota to the patient.

* * * * *

SEQUENCE LISTING

```
<160> NUMBER OF SEQ ID NOS: 21

<210> SEQ ID NO 1
<211> LENGTH: 418
<212> TYPE: DNA
<213> ORGANISM: Alloprevotella
<220> FEATURE:
<221> NAME/KEY: misc_feature
<222> LOCATION: (1)..(418)
<223> OTHER INFORMATION: Representative sequence.

<400> SEQUENCE: 1
aggaatattg gtcaatggac ggaagtctga accagccaag tagcgtgcag gatgacggcc        60
ctctgggttg taaactgctt ttagttggga ataaaaaaga ggacgtgtcc tctattgtat       120
gtaccttcag aaaaaggacc ggctaattcc gtgccagcag ccgcggtaat acggaaggtc       180
caggcgttat ccggatttat tgggtttaaa gggagcgtag gcggattatt aagtcagtgg       240
tgaaagacgg tggctcaacc atcgttagcc attgaaactg gtagtcttga gtgcagacag       300
ggatgctgga actcgtggtg tagcggtgaa atgcttagat atgacgaaga actccgattg       360
cgaaggcagc tgacgggagc gcaactgacg cttaagctcg aaggtgcggg tatcaaac        418

<210> SEQ ID NO 2
<211> LENGTH: 418
<212> TYPE: DNA
<213> ORGANISM: Alloprevotella
<220> FEATURE:
<221> NAME/KEY: misc_feature
<222> LOCATION: (1)..(418)
<223> OTHER INFORMATION: Representative sequence

<400> SEQUENCE: 2
aggaatattg gtcaatggac ggaagtctga accagccaag tagcgtgcag gatgacggcc        60
ctctgggttg taaactgctt ttagttggga ataaaaaaga ggacgtgtcc tctattgtat       120
gtaccttcag aaaaaggacc ggctaattcc gtgccagcag ccgcggtaat acggaaggtc       180
caggcgttat ccggatttat tgggtttaaa gggagcgtag gcggattatt aagtcagtgg       240
```

-continued

```
tgaaagacgg tggctcaacc atcgttagcc attgaaactg gtagtcttga gtgcagacag      300
ggatgctgga actcgtggtg tagcggtgaa atgcttagat atcacgatga actccaatcg      360
cgaaggcagg tgtccgggct gcaactgacg ctgaggctcg aaagtgtggg tatcaaac       418

<210> SEQ ID NO 3
<211> LENGTH: 418
<212> TYPE: DNA
<213> ORGANISM: Alloprevotella
<220> FEATURE:
<221> NAME/KEY: misc_feature
<222> LOCATION: (1)..(418)
<223> OTHER INFORMATION: Representative sequence

<400> SEQUENCE: 3
aggaatattg gtcaatggac ggaagtctga accagccaag tagcgtgcag gatgacggcc       60
ctctgggttg taaactgctt ttagttggga ataaaaaaga ggacgtgtcc tctattgtat      120
gtaccttcag aaaaaggacc ggctaattcc gtgccagcag ccgcggtaat acggaaggtc      180
caggcgttat ccggatttat tgggtttaaa gggagcgtag gcggattatt aagtcagtgg      240
tgaaagacgg tggctcaacc atcgttagcc attgaaactg gtagtcttga gtgcagacag      300
ggatgctgga actcgtggtg tagcggtgaa atgcttagat atcacgatga actccgatcg      360
cgaaggcagg tgtccgggct gcaactgacg ctgaggctcg aaagtgtggg tatcaaac       418

<210> SEQ ID NO 4
<211> LENGTH: 400
<212> TYPE: DNA
<213> ORGANISM: Prevotella
<220> FEATURE:
<221> NAME/KEY: misc_feature
<222> LOCATION: (1)..(400)
<223> OTHER INFORMATION: Representative sequence

<400> SEQUENCE: 4
gggaatattg cacaatgggg gaaaccctga tgcagcaacg ccgcgtgaac gatgaaggcc       60
tttgggtcgt aaagttctgt tctaggtgat gaaaactgac agtaacctag gagaaagccc      120
cggctaactc cgtgccagca gccgcggtaa tacggagggg gcaagcgtta tccggattta      180
ttgggtttaa agggagcgta ggccgtagat taagcgtgtt gtgaaatgta gatgctcaac      240
atctgacttg cagcgcgaac tggttttactt gagtgtgcgc aacgtaggcg gaattcgtcg      300
tgtagcggtg aaatgcttag atatgacgaa gaactccgat tgcgaaggca gcttacggga      360
gcacaactga cgctgaagct cgaaggtgcg ggtatcaaac                            400

<210> SEQ ID NO 5
<211> LENGTH: 397
<212> TYPE: DNA
<213> ORGANISM: Prevotella
<220> FEATURE:
<221> NAME/KEY: misc_feature
<222> LOCATION: (1)..(397)
<223> OTHER INFORMATION: Representative sequence.

<400> SEQUENCE: 5
gggaatattg cacaatggag gaaactctga tgcagtgaca ccgcgtatag gaagaaggtc       60
ttaggattgt aagctattgt cgtgtgagaa gaaaatgacc atcacaggag gaagccctgg      120
ctaaatatgt gccagcagcc gcggtaatac ggaaggtccg ggcgttatcc ggatttattg      180
ggtttaaagg gagcgtaggc cgtggattaa gcgtgttgtg aaatgcaggt gctcaacgtc      240
tgcactgcag cgcgaactgg ttcacttgag tgtgcacaac gcaggcggaa ttcgtcgtgt      300
```

```
agcggtgaaa tgcttagata tgacgaagaa ctccgattgc gaaggcagct tgcgggagca      360
caactgacgc tgaagctcga aagtgcgggt atcgaac                               397

<210> SEQ ID NO 6
<211> LENGTH: 402
<212> TYPE: DNA
<213> ORGANISM: Prevotella
<220> FEATURE:
<221> NAME/KEY: misc_feature
<222> LOCATION: (1)..(402)
<223> OTHER INFORMATION: Representative sequence

<400> SEQUENCE: 6
gggaatattg dacaatgggg gcaaccctga tccagcaatt ctgtgtgcac gatgaaggtc       60
ttcggattgt aaagtgcttt cagcagggaa gaaaaaaatg acggtacctg cagaagaagc      120
gacggctaaa tacgtgccag cagccgcggt aatacggaag gtccaggcgt tatccggatt      180
tattgggttt aaagggagtg taggcggttt gttaagcgtg ttgtgaaatt tagatgctca      240
acatttaact tgcagcgcga actgtcagac ttgagtacac gcaacgtatg cggaattcat      300
ggtgtagcgg tgaaatgctt agatatcatg aagaactccg attgcgaagg cagcatacgg      360
gagtgtaact gacgcttaag ctcgaaggtg cgggtatcga ac                         402

<210> SEQ ID NO 7
<211> LENGTH: 400
<212> TYPE: DNA
<213> ORGANISM: Campylobacter
<220> FEATURE:
<221> NAME/KEY: misc_feature
<222> LOCATION: (1)..(400)
<223> OTHER INFORMATION: Representative sequence

<400> SEQUENCE: 7
gggaatattg ctcaatgggg gaaaccctga agcagcaacg ccgcgtggag gatgacactt       60
ttcggagcgt aaactccttt tcttggggaa gaaatttgac ggtacccaag gaataagcac      120
cggctaactc cgtgccagca gccgcggtaa tacggagggt gcaagcgtta ctcggaatca      180
ctgggcgtaa aggacgcgta ggcggattat caagtctctt gtgaaatcca atggcttaac      240
cattgaactg cttgggaaac tgataatcta gagtgaggga gaggcagatg gaattggtgg      300
tgtaggggta aaatccgtag agatcaccag gaatacccat tgcgaaggcg atctgctgga      360
actcaactga cgctaatgcg tgaaagcgtg gggagcaaac                            400

<210> SEQ ID NO 8
<211> LENGTH: 400
<212> TYPE: DNA
<213> ORGANISM: Campylobacter
<220> FEATURE:
<221> NAME/KEY: misc_feature
<222> LOCATION: (1)..(400)
<223> OTHER INFORMATION: Representative sequence

<400> SEQUENCE: 8
gggaatattg ctcaatgggg gaaaccctga agcagcaacg ccgcgtggag gatgacactt       60
ttcggagcgt aaactccttt tcttggggaa gaaatttgac ggtacccaag gaataagcac      120
cggctaactc cgtgccagca gccgcggtaa tacggagggt gcaagcgtta ctcggaatca      180
ctgggcgtaa aggacgcgta ggcggattat caagtctctt gtgaaatcca atggcttaac      240
cattgaactg cttgggaaac tgataatcta gagtgaggga gaggcagatg gaattggtgg      300
```

```
tgtaggggta aaatccgtag agatcaccag gaatacccat tgcgaaggcg atctgctgga      360
actcaactga cgctaatgcg cgaaagcgtg gggagcaaac                            400

<210> SEQ ID NO 9
<211> LENGTH: 400
<212> TYPE: DNA
<213> ORGANISM: Campylobacter
<220> FEATURE:
<221> NAME/KEY: misc_feature
<222> LOCATION: (1)..(400)
<223> OTHER INFORMATION: Representative sequence

<400> SEQUENCE: 9
gggaatattg ctcaatgggg gaaaccctga agcagcaacg ccgcgtggag gatgacactt       60
ttcggagcgt aaactccttt tcttaggaaa gaattatgac ggtacctaag gaataagcac      120
cggctaactc cgtgccagca gccgcggtaa tacgggggggt gcaagcgtta ctcggaatca      180
ctgggcgtaa aggacgcgta ggcggattat caagtctctt gtgaaattta acggcttaac      240
cgttaaactg cttgggaaac tgataatcta gagtaaggga gaggcagatg gaattcttgg      300
tgtaggggta aaatccgtag agatcaagaa gaatacttat tgcgaaggcg atctgctaga      360
acttaactga cgctaatgcg tgaaagcgtg gggagcaaac                            400

<210> SEQ ID NO 10
<211> LENGTH: 405
<212> TYPE: DNA
<213> ORGANISM: Rothia
<220> FEATURE:
<221> NAME/KEY: misc_feature
<222> LOCATION: (1)..(405)
<223> OTHER INFORMATION: Representative sequence

<400> SEQUENCE: 10
gggaatcttc ggcaatggac ggaagtctga ccgagcaacg ccgcgtgagt gaagaaggtt       60
ttcggatcgt aaagctctgt tagcagggaa gaagagagat tgacggtacc tgcagagaaa      120
gcgccggcta actacgtgcc agcagccgcg gtaatacgta gggcgcgagc gttgtccgga      180
attattgggc gtaaagagct tgtaggcggt ttgtcgcgtc tgctgtgaaa ggccggagct      240
taactccgtg tattgcagtg ggtacgggca gactagagtg cagtagggga gactggaact      300
cctggtgtag cggtggaatg cgcagatatc aggaagaaca ccgatggcga aggcaggtct      360
ctgggctgta actgacgctg agaagcgaaa gcatggggag cgaac                      405

<210> SEQ ID NO 11
<211> LENGTH: 406
<212> TYPE: DNA
<213> ORGANISM: Rothia
<220> FEATURE:
<221> NAME/KEY: misc_feature
<222> LOCATION: (1)..(406)
<223> OTHER INFORMATION: Representative sequence

<400> SEQUENCE: 11
aggaatattg gtcaatgggc gcgagcctga accagccaag tagcgtgcag gatgacggcc       60
ctatgggttg taaacctctg ttagcaggga agaagagaga ttgacggtac ctgcagagaa      120
agcgccggct aactacgtgc cagcagccgc ggtaatacgt agggcgcgag cgttgtccgg      180
aattattggg cgtaaagagc ttgtaggcgg tttgtcgcgt ctgctgtgaa aggccggagc      240
ttaactccgt gtattgcagt gggtacgggc agactagagt gcagtagggg agactggaat      300
```

-continued

```
tcctggtgta gcggtggaat gcgcagatat caggaggaac accgatggcg aaggcaggtc      360
tctgggctgt aactgacgct gagaagcgaa agcatgggga gcgaac                    406

<210> SEQ ID NO 12
<211> LENGTH: 405
<212> TYPE: DNA
<213> ORGANISM: Rothia
<220> FEATURE:
<221> NAME/KEY: misc_feature
<222> LOCATION: (1)..(405)
<223> OTHER INFORMATION: Representative sequence

<400> SEQUENCE: 12
gggaatattg cacaatgggc gcaagcctga tgcagcgacg ccgcgtgagg gatgacggcc       60
ttcgggttgt aaacctctgt tagcagggaa gaagagagat tgacggtacc tgcagagaaa      120
gcgccggcta actacgtgcc agcagccgcg gtaatacgta gggcgcgagc gttgtccgga      180
attattgggc gtaaagagct tgtaggcggt ttgtcgcgtc tgctgtgaaa ggccggagct      240
taactccgtg tattgcagtg ggtacgggca gactagagtc agtaggggga gactggaatt      300
cctggtgtag cggtgaaatg cgtagatatt aggaagaaca ccagtggcga aggcgacttt      360
ctggacgaaa actgacgctg aggcgcgaaa gccaggggag cgaac                     405

<210> SEQ ID NO 13
<211> LENGTH: 399
<212> TYPE: DNA
<213> ORGANISM: Catonella
<220> FEATURE:
<221> NAME/KEY: misc_feature
<222> LOCATION: (1)..(399)
<223> OTHER INFORMATION: Representative sequence

<400> SEQUENCE: 13
ggggatattg cacaatggag gaaactctga tgcagcgacg ccgcgtgagt gaagaagtgc       60
tccggcatgt aaagctcttt cagcagggaa gatgatgacg gtacctgaat aagaagcccc      120
ggctaactac gtgccagcag ccgcggtaat acgtaggggg caagcgttat ccggatttac      180
tgggtgtaaa gggagcgcag gcggtctggc aagttgagag tggaagcagg gggctcaacc      240
ccctgactgc tcccaaaact gttggactgg agtatgggag aggcaggcgg aattcctagt      300
gtagcggtga aatgctcaga tattaggaag aacaccggtg gcgaaggcgg cctgctggac      360
caaaactgac gctgaggctc gagagcgtgg ggagcgaac                           399

<210> SEQ ID NO 14
<211> LENGTH: 399
<212> TYPE: DNA
<213> ORGANISM: Catonella
<220> FEATURE:
<221> NAME/KEY: misc_feature
<222> LOCATION: (1)..(399)
<223> OTHER INFORMATION: Representative sequence

<400> SEQUENCE: 14
ggggatattg cacaatggag gaaactctga tgcagcgacg ccgcgtgagt gaagaagtat       60
ttcggtatgt aaagctctat cagcagggaa gatgatgacg gtacctgact aagaagcccc      120
ggctaactac gtgccagcag ccgcggtaat acgtaggggg caagcgttat ccggatttac      180
tgggtgtaaa gggagcgcag gcggtttttgc aagttgagag tggaagcagg gggctcaacc      240
ccttgactgc tcccaaaact gtaaaacttg agtgtagatg aggtaggcgg aatgcgtggt      300
```

-continued

```
gtagcggtgg aatgcataga tatcacgcag aactccgatt gcgaaggcag cttactaagg      360
tacaactgac gctgaagcac gaaagcgtgg gtatcaaac                             399

<210> SEQ ID NO 15
<211> LENGTH: 399
<212> TYPE: DNA
<213> ORGANISM: Catonella
<220> FEATURE:
<221> NAME/KEY: misc_feature
<222> LOCATION: (1)..(399)
<223> OTHER INFORMATION: Representative sequence

<400> SEQUENCE: 15
ggggatattg cacaatggag gaaactctga tgcagcgacg ccgcgtgagt gaagaagtat       60
ttcggtatgt aaagctctat cagcagggaa gatgatgacg gtacctgact aagaagcccc      120
ggctaactac gtgccagcag ccgcggtaat acgtaggggg caagcgttat ccggatttac      180
tgggtgtaaa gggagcgcag gcggtttttgc aagttgagag tggaagcagg gggctcaacc     240
ccctgactgc tcccaaaact gtaaaacttg agtatgggag aggcaggcgg aattcctagt      300
gtagcggtga aatgcttaga tattaggaag aacaccggtg gcgaaggcgg cctgctggac      360
caaaactgac gctgaggctc gaaagcgtgg gtagcaaac                             399

<210> SEQ ID NO 16
<211> LENGTH: 418
<212> TYPE: DNA
<213> ORGANISM: Porphyromona
<220> FEATURE:
<221> NAME/KEY: misc_feature
<222> LOCATION: (1)..(418)
<223> OTHER INFORMATION: Representative sequence

<400> SEQUENCE: 16
aggaatattg gtcaatgggc gagagcctga accagccaag tcgcgtgaag gatgactgtc       60
ttatggattg taaacttctt ttatacggga ataacaagag ccacgtgtgg ctccctgcat      120
gtaccgtatg aataagcatc ggctaactcc gtgccagcag ccgcggtaat acggaggatg      180
cgagcgttat ccggatttat tgggtttaaa gggtgcgtag gcggcctgtt aagtaagtgg      240
ttaaattgtt gggctcaacc caatccagcc acttaaactg gcaggctaga gtattggaga      300
ggcaagtgga attccatgtg tagcggtaaa atgcgtagat atatggagga ataccgatgg      360
cgaaggcagc ctcctgggat aacactgacg ttcatgctcg aaagcgtggg tagcaaac       418

<210> SEQ ID NO 17
<211> LENGTH: 418
<212> TYPE: DNA
<213> ORGANISM: Porphyromona
<220> FEATURE:
<221> NAME/KEY: misc_feature
<222> LOCATION: (1)..(418)
<223> OTHER INFORMATION: Representative sequence

<400> SEQUENCE: 17
aggaatcttc cacaatgggc gaaagcctga tggagcaacg ccgcgtgaag gatgaaggcc       60
ttcgggttgt aaacttcttt tgtaggggaa taaagaatgg tacgtgtacc atagtgaatg      120
taccctacga ataagcatcg gctaactccg tgccagcagc cgcggtaata cggaggatgc      180
gagcgttatc cggatttatt gggtttaaag ggtgcgtagg cggcctgtta agtcagcggt      240
gaaatctagg ggcttaactc ctaaattgcc attgatactg gtgggcttga gtgtagatga      300
```

```
ggtaggcgga atgcgtggtg tagcggtgga atgcatagat atcacgcaga actccaattg      360
cgaaggcagc ttactaaggt acaactgacg ctgaagcacg aaagcgtggg tatcaaac       418

<210> SEQ ID NO 18
<211> LENGTH: 399
<212> TYPE: DNA
<213> ORGANISM: Porphyromona
<220> FEATURE:
<221> NAME/KEY: misc_feature
<222> LOCATION: (1)..(399)
<223> OTHER INFORMATION: Representative sequence

<400> SEQUENCE: 18
gggaatattg cacaatgggg gaaaccctga tgcagcgacg ccgcgtgagt gaagaagtat       60
ttcggtatgt aaagctctat cagcagggaa gataatgaca gtacctgact aagaagcccc      120
ggctaactac gtgccagcag ccgcggtaat acggaggatg cgagcgttat ccggatttat      180
tgggtttaaa gggtgcgtag gcggcctgtt aagtcagcgg tgaaatctag gagcttaact      240
cctaaattgc cattgatact ggcgggcttg agtgtagatg aggtaggcgg aatgcgtggt      300
gtagcggtgg aatgcataga tatcacgcag aactccgatt gcgaaggcag cttactaagg      360
tacaactgac gctgaagcac gaaagcgtgg gtatcaaac                             399

<210> SEQ ID NO 19
<211> LENGTH: 401
<212> TYPE: DNA
<213> ORGANISM: Fretibacterium
<220> FEATURE:
<221> NAME/KEY: misc_feature
<222> LOCATION: (1)..(401)
<223> OTHER INFORMATION: Representative sequence

<400> SEQUENCE: 19
gggaatattg ggcaatggga ggaatcctga cccagcgacg ccgcgtgaac gaagacggcc       60
ttcgggttgt aaagttcttt tatgtgggaa gaatgaagtg acggtaccac atgaataagc      120
cccggctaac tacgtgccag cagccgcggt aatacgtagg gggcgagcgt tgtccggaat      180
tactgggcgt aaagggcacg caggctgtgc ttcaagtcag ctgtaaaagg atgcggctta      240
accgtgttat gcggctgaga ctgaggtgct ggagtaccgg agaggcaagt ggaattccca      300
gtgtagcggt gaaatgcgta gatattggga agaacatcgg tggcgaaggc gacttgctgg      360
acggtaactg acgctgaggt gcgaaagcca gggtagcgaa c                         401

<210> SEQ ID NO 20
<211> LENGTH: 401
<212> TYPE: DNA
<213> ORGANISM: Fretibacterium
<220> FEATURE:
<221> NAME/KEY: misc_feature
<222> LOCATION: (1)..(401)
<223> OTHER INFORMATION: Representative sequence

<400> SEQUENCE: 20
gggaatattg ggcaatggga ggaatcctga cccagcgacg ccgcgtgaac gaagacggcc       60
ttcgggttgt aaagttcttt tatgtgggaa gaaggaagtg acggtaccac atgaataagc      120
cccggctaac tacgtgccag cagccgcggt aatacgtagg gggcgagcgt tgtccggaat      180
tactgggcgt aaagggcacg caggctgtgc ttcaagtcag ctgtaaaagg atgcggctta      240
accgtgttat gcggctgaga ctgaggtgct ggagtaccgg agaggcaagt ggaattccca      300
```

-continued

```
gtgtagcggt gaaatgcgta gatattggga agaacatcgg tggcgaaggc gacttgctgg      360
acggtaactg acgctgaggt gcgaaagcca gggtagcgaa c                           401

<210> SEQ ID NO 21
<211> LENGTH: 401
<212> TYPE: DNA
<213> ORGANISM: Fretibacterium
<220> FEATURE:
<221> NAME/KEY: misc_feature
<222> LOCATION: (1)..(401)
<223> OTHER INFORMATION: Representative sequence

<400> SEQUENCE: 21
gggaatattg ggcaatggga ggaatcctga cccagcgacg ccgcgtgaac gaagacggcc       60
ttcgggttgt aaagttcttt tatgtgggaa gaataaagtg acggtaccac atgaataagc      120
cccggctaac tacgtgccag cagccgcggt aatacgtagg gggcgagcgt tgtccggaat      180
tactgggcgt aaagggcacg caggctgtgc ttcaagtcag ctgtaaaagg atgcggctta      240
accgtgttat gcagttgaga ctgaggtgct ggagtaccgg agaggcaagt ggaattccca      300
gtgtagcggt gaaatgcgta gatattggga agaacatcgg tggcgaaggc gacttgctgg      360
acggtaactg acgctgaggt gcgaaagcca gggtagcgaa c                           401
```